(12) United States Patent
Sprott et al.

(10) Patent No.: US 6,420,592 B1
(45) Date of Patent: Jul. 16, 2002

(54) AMINO ACID-DERIVED PHOSPONAMIDIC ANHYDRIDES AND METHODS OF PREPARING THE SAME

(75) Inventors: Kevin T. Sprott; Paul R. Hanson, both of Lawrence, KS (US)

(73) Assignee: University of Kansas, Lawrence, KS (US)

( * ) Notice: Subject to any disclaimer, the term of this patent is extended or adjusted under 35 U.S.C. 154(b) by 31 days.

(21) Appl. No.: 09/639,050

(22) Filed: Aug. 15, 2000

(51) Int. Cl.$^7$ .............................. C07C 69/66; C07F 9/02
(52) U.S. Cl. .................. 560/168; 560/169; 560/174; 562/878
(58) Field of Search .................. 562/878; 560/174, 560/168, 169

(56) References Cited

U.S. PATENT DOCUMENTS

| | | | | |
|---|---|---|---|---|
| 2,502,966 A | * | 4/1950 | Kosolapoff | 562/878 |
| 3,248,458 A | * | 4/1966 | Ofrtel et al. | 562/878 |
| 3,329,687 A | | 7/1967 | Houlihan | |
| 3,366,714 A | * | 1/1968 | Popoff | 562/878 |
| 3,972,866 A | * | 8/1976 | Fortuin | 526/77 |
| 5,312,940 A | | 5/1994 | Grubbs et al. | 556/136 |
| 5,342,909 A | | 8/1994 | Grubbs et al. | 526/171 |
| 5,506,355 A | | 4/1996 | Jadhav et al. | 540/545 |
| 5,610,294 A | | 3/1997 | Lam et al. | 540/492 |
| 5,710,298 A | | 1/1998 | Grubbs et al. | 556/22 |
| 5,750,815 A | | 5/1998 | Grubbs et al. | 585/511 |
| 5,917,071 A | | 6/1999 | Grubbs et al. | 556/21 |
| 6,048,993 A | | 4/2000 | Grubbs et al. | 556/21 |

FOREIGN PATENT DOCUMENTS

| | | |
|---|---|---|
| WO | 9419329 | 9/1994 |
| WO | 9937643 | 7/1999 |

OTHER PUBLICATIONS

Zhu, S. et al., "Chiral Mo–Binol Complexes: Activity, Synthesis, and Structure, Efficient Enantioselective Six–Membered Ring Synthesis Through Catalytic Metathesis" *J. Am. Chem. Soc.*, 1999, 121, 8251–8259.

Kingsbury, J. et al., "A Recyclable Ru–Based Metathesis Catalyst", *J. Am. Chem. Soc.*, 1999, 121, 791–799.

Scholl, M. et al., "Synthesis and Activity of a New Generation of Ruthenium–Based Olefin Metathesis Catalysts Coordinated With 1,3–Dimesityl–4,5–dihydroimidazol–2–ylidene Ligands§", *Org. Lett.*, vol. 1, No. 6, 1999, 953–956.

Totland, K. et al., "Ring Opening Metathesis Polymerization With Binaphtholate or Biphenolate Complexes of Molybdenum", *Macromolecules*, 1996, 29, 6114–6125.

Alexander, J. et al., "Catalytic Enantioselective Ring–Closing Metathesis by a Chiral Biphen–Mo Complex", *J. Am. Chem. Soc.*, 1998, 120, 4041–4042.

Bäckbro, K., "Unexpected Binding Mode of Cyclic Sulfamide HIV–1 Protease Inhibitor", *J. Med. Chem.*, 1997, 40, 898–902.

Hultén, J. et al., "Inhibitors of the $c_2$–Symmetric HIV–1 Protease: Nonsymmetric Binding of a Symmetric Cyclic Sulfamide With Ketoxime Groups in the P2/P2' Side Chains", *J. Med. Chem.*, 1999, 42, 4054–4061.

\* cited by examiner

*Primary Examiner*—Floyd D. Higel
*Assistant Examiner*—Ebenezer Sackey
(74) *Attorney, Agent, or Firm*—Hovey Williams LLP

(57) ABSTRACT

Phosphonamide compounds and methods of forming those compounds are provided. The inventive methods comprise forming a template opened-ring phosphonamide compound and optionally subjecting the template to a ring-closing metathesis reaction in the presence of a ring-closing catalyst (e.g., a Grubbs catalyst) to yield a heterocyclic phosphonamide. Advantageously, the template structures can be provided with a wide array of functional groups (e.g., amino acid side chains, peptides) chosen to provide particular properties to the compound. The preferred heterocyclic phosphonamides are represented by the formula

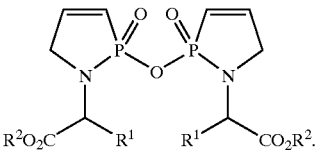

20 Claims, No Drawings

AMINO ACID-DERIVED PHOSPONAMIDIC ANHYDRIDES AND METHODS OF PREPARING THE SAME

BACKGROUND OF THE INVENTION

1. Field of the Invention

The present invention is directed towards new phosphonamidic anhydrides and methods of forming those compounds. The compounds have a number of uses including as inhibitors of enzymes and regulators of plant growth.

2. Description of the Prior Art

Small peptides are excellent starting points for drug design because they have the potential to overcome the pharmacokinetic shortcomings of larger peptides, yet retain the desirable quality of molecular recognition. A number of dipeptides are currently being developed as novel pharmaceutical agents (see e.g., Blackburn et al., *Bioorg. Med. Chem. Lett.*, 7:823–26 (1997); Schullek et al., *Anal. Biochem.*, 246:20–29 (1997), each incorporated by reference herein). Unfortunately, even small peptides suffer from proteolytic instability which limits their use as drug candidates.

Anhydrides and their derivatives have a rich history both in terms of their synthetic utility as well as their biological relevance (see e.g., Tarbell, *Accounts Chem. Res.*, 2:296–300 (1969); Martin et al., *Chem.*, 27:90–95 (1987), each incorporated by reference herein). Anhydrides are widely known to serve as potent inhibitors of a variety of enzymes (see e.g., Karibian et al., *Biochemistry*, 13:2891 (1974), incorporated by reference herein), with a number of anhydrides recently being reported as effective inactivators of various serine proteases (see e.g., Iijima et al., *Biorg. Med. Chem. Lett.*, 9:413 (1999), incorporated by reference herein).

Pyrophosphate and related analogs are a class of phosphorus-based anhydrides that have gained attention for their ability to inhibit osteoclastic bone resorption, and therefore are useful therapeutic agents to treat and prevent osteoporosis (see e.g., Sato et al., *J. Med. Chem.*, 42:1 (1999), incorporated by reference herein). Biphosphonates, synthetic nonhydrolyzable P—C—P analogs of pyrophosphates, are highly effective agents for inhibiting osteoclastic bone resorption (see e.g., Russell et al., *Bone*, 25:97 (1999); Teronen et al., *Ann. N.Y. Acad. Sci.*, 878:453–65 (1999), each incorporated by reference herein). Biphosphonic acids have also proven to be effective inhibitors of squalene synthase, a crucial enzyme in the role of cholesterol biosynthesis. Thus, there is a need to develop new pyrophosphate analogs which improve the therapeutic properties of biphosphonates.

SUMMARY OF THE INVENTION

The present invention is broadly concerned with new phosphonamide compounds and methods of forming such compounds.

In more detail, the compounds are phosphonamidic anhydrides, and more particularly chiral phosphonamidic anhydrides. The preferred compounds are represented by a formula selected from the group consisting of

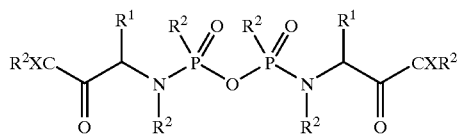

and

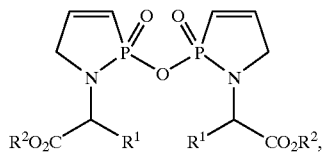

wherein:

each X is individually selected from the group consisting of oxygen, —NH, and —NOR$^1$;

each R$^1$ is individually selected from the group consisting of hydrogen, substituted and unsubstituted amino acid side chains, and 2–15 mer peptides; and each R$^2$ is individually selected from the group consisting of hydrogen, branched and unbranched alkyl groups (preferably C$_1$–C$_{18}$, more preferably C$_1$–C$_8$), branched and unbranched alkenyl groups (preferably C$_2$–C$_{18}$, more preferably C$_2$–C$_8$), branched and unbranched alkynyl groups (preferably C$_2$–C$_{18}$, more preferably C$_2$–C$_8$), allyl groups, acyl groups (preferably C$_2$–C$_{18}$, more preferably C$_2$–C$_8$) aryl groups (preferably C$_6$–C$_{12}$), 2–15 mer peptides, and benzyl groups.

Preferably at least one R$^1$ group comprises an amino acid side chain selected from the group consisting of

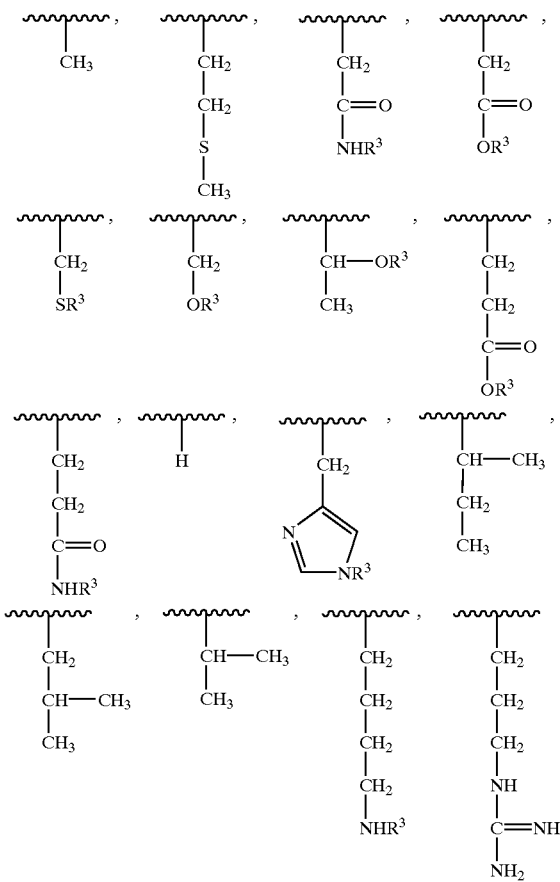

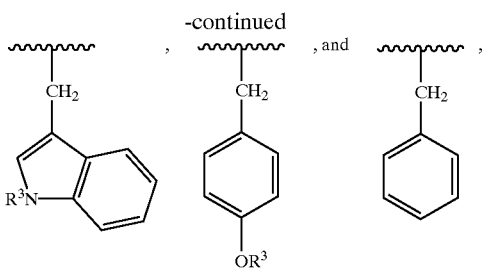

wherein each $R^3$ is individually selected from the group consisting of hydrogen, branched and unbranched alkyl groups (preferably $C_1$–$C_{18}$, more preferably $C_1$–$C_8$), branched and unbranched alkenyl groups (preferably $C_2$–$C_{18}$, more preferably $C_2$–$C_8$), branched and unbranched alkynyl groups (preferably $C_2$–$C_{18}$, more preferably $C_2$–$C_8$), allyl groups, aryl groups (preferably $C_6$–$C_{12}$), acyl groups (preferably $C_2$–$C_{18}$, more preferably $C_2$–$C_8$), and benzyl groups.

In a preferred embodiment, each $R^1$ is individually selected from the group consisting of —$CH_3$, —$CH_2CH(R^4)_2$, —$CH_2R^4$, and —$CH(R^4)_2$, with each $R^4$ being individually selected from the group consisting of alkyl groups (preferably methyl), aryl groups (preferably phenyl), and benzyl groups, and each $R^2$ is individually selected from the group consisting of —$CH_3$ and —$CHCH_2$. Two particularly preferred compounds according to the invention comprise a formula selected from the group consisting of

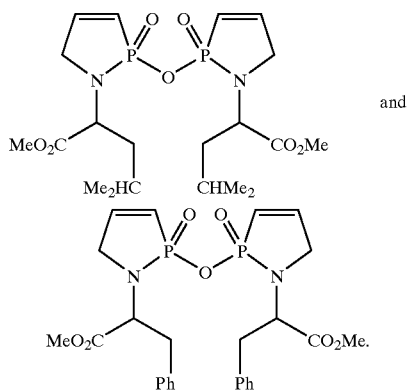

and

The inventive compounds are formed by reacting an allylated compound with a phosphonic compound to form an intermediate compound which is the dimerized. Preferred allylated compounds comprise the formula

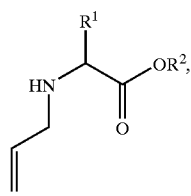

wherein:
  $R^1$ is selected from the group consisting of hydrogen, substituted and unsubstituted amino acid side chains, and 2–15 mer peptides; and
  $R^2$ is selected from the group consisting of hydrogen, branched and unbranched alkyl groups (preferably $C_1$–$C_{18}$, more preferably $C_1$–$C_8$), branched and unbranched alkenyl groups (preferably $C_2$–$C_{18}$, more preferably $C_2$–$C_8$), branched and unbranched alkynyl groups (preferably $C_2$–$C_{18}$, more preferably $C_2$–$C_8$), allyl groups, aryl groups (preferably $C_6$–$C_{12}$), acyl groups (preferably $C_2$–$C_{18}$, more preferably $C_2$–$C_8$), 2–15 mer peptides, and benzyl groups.

Preferred phosphonic compounds comprise the formula $R^4POY_2$, wherein:
  $R^4$ is selected from the group consisting of hydrogen, branched and unbranched alkyl groups (preferably $C_1$–$C_{18}$, more preferably $C_1$–$C_8$), branched and unbranched alkenyl groups (preferably $C_2$–$C_{18}$, more preferably $C_2$–$C_8$), branched and unbranched alkynyl groups (preferably $C_2$–$C_{18}$, more preferably $C_2$–$C_8$), allyl groups, aryl groups (preferably $C_6$–$C_{12}$), acyl groups (preferably $C_2$–$C_{18}$, more preferably $C_2$–$C_8$), 2–15 mer peptides, and benzyl groups; and
  each Y is individually selected from the group consisting of the halogens.

The intermediate compound comprises a formula selected from the group consisting of

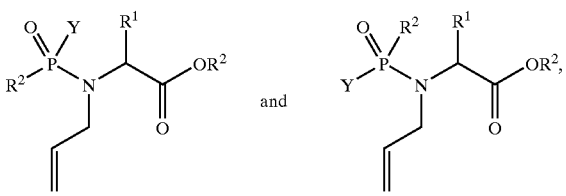

wherein:
  $R^1$ is selected from the group consisting of hydrogen, substituted and unsubstituted amino acid side chains, and 2–15 mer peptides;
  $R^2$ is selected from the group consisting of hydrogen, branched and unbranched alkyl groups (preferably $C_1$–$C_{18}$, more preferably $C_1$–$C_8$), branched and unbranched alkenyl groups (preferably $C_2$–$C_{18}$, more preferably $C_2$–$C_8$), branched and unbranched alkynyl groups (preferably $C_2$–$C_{18}$, more preferably $C_2$–$C_8$), allyl groups, aryl groups (preferably $C_6$–$C_{12}$), acyl groups (preferably $C_2$–$C_{18}$, more preferably $C_2$–$C_8$), 2–15 mer peptides, and benzyl groups; and
  each Y is individually selected from the group consisting of the halogens.

Preparing the phosphonamide compounds according to the inventive methods results in a yield of those compounds of at least about 70%, and preferably at least about 95%, wherein the theoretical yield is taken as 100%.

Optionally, the phosphonamide compound can be subjected to a ring-closing metathesis reaction in the presence of a ring-closing catalyst to yield a bicyclic phosphonamide. Preferred ring-closing catalysts are olefin metathesis catalysts such as Grubbs catalysts (see e.g., U.S. Pat. Nos. 6,048,993, 5,917,071, 5,750,815, 5,710,298, 5,342,909, and 5,312,940, each incorporated by reference herein) as well as those disclosed by the following references, each also incorporated by reference herein: Matthias, *Org. Ltrs.*, 1(6):953–56 (1999); Schrock, *Macromolecules*, 29(19):6114–25 (1996); Zhu et al., *J. Amer. Chem. Soc.*, 121(36):8251–59 (1999); Alexander et al., *J. Amer. Chem. Soc.*, 120(16):4041–42 (1998); and Kingsbury et al., *J. Amer. Chem. Soc.*, 121(4):791–99 (1999).

Particularly preferred Grubbs catalysts are those selected from the group consisting of

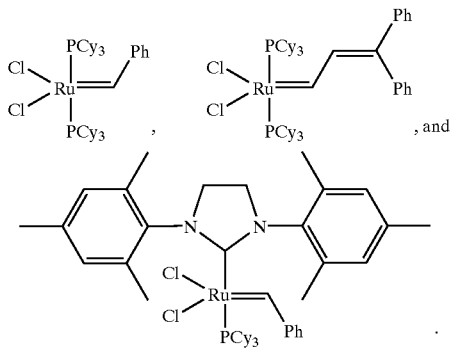

Preferably the reacting step is carried out at a temperature of from about 15–80° C., and more preferably from about 30–55° C. Furthermore, the reacting step should be carried out in a solvent system comprising a solvent selected from the group consisting of toluene, benzene, chlorobenzene, dichlorobenzene, methylene chloride, dimethoxyethane (DME), and mixtures thereof.

It will be appreciated that the inventive methods allow for the synthesis of a wide array of both symmetric and unsymmetric cyclic and acyclic phosphonamide compounds. Furthermore, the inventive methods allow for preparation of, or selection of, templates having particular functional groups bonded thereto which are then readily formed into the desired phosphonamide in a controlled and repeatable manner. Because the method can be adapted to form phosphonamide compounds comprising one or more amino acid side chains or peptides bonded thereto, the inventive compounds can be used to inhibit enzymes (such as squalene synthetase), to act as osteoporitic agents, and to regulate plant growth.

DETAILED DESCRIPTION OF THE PREFERRED EMBODIMENTS

EXAMPLES

The following examples set forth preferred methods in accordance with the invention. It is to be understood, however, that these examples are provided by way of illustration and nothing therein should be taken as a limitation upon the overall scope of the invention.

A number of abbreviations are used herein. These abbreviations and the term or terms that they represent are set forth in Table A.

TABLE A

| Abbreviation | Term(s) |
| --- | --- |
| hex | hexane |
| Bn | benzyl |
| Ph | phenyl |
| Me | methyl |
| Et | ethyl |
| Boc | butoxy carbonyl |
| EtOAc | ethyl acetate |
| Et$_3$N | triethyl amine |
| $^t$BuO | tert-butoxy |

Grubbs Catalysts were used in some of the following Examples. These catalysts are referred to as follows:

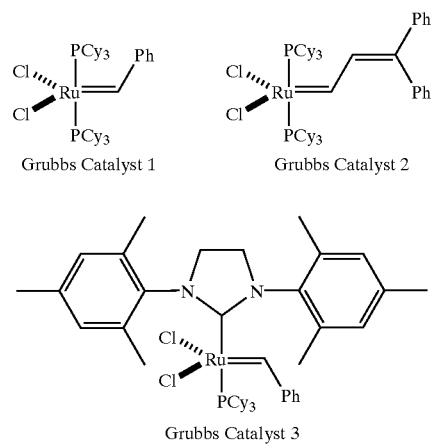

Grubbs Catalyst 1    Grubbs Catalyst 2

Grubbs Catalyst 3

Example 1

Scheme A depicts the general overall reaction scheme followed in Parts I–II below, as well as the various compounds which can be prepared according to the procedure described in this example.

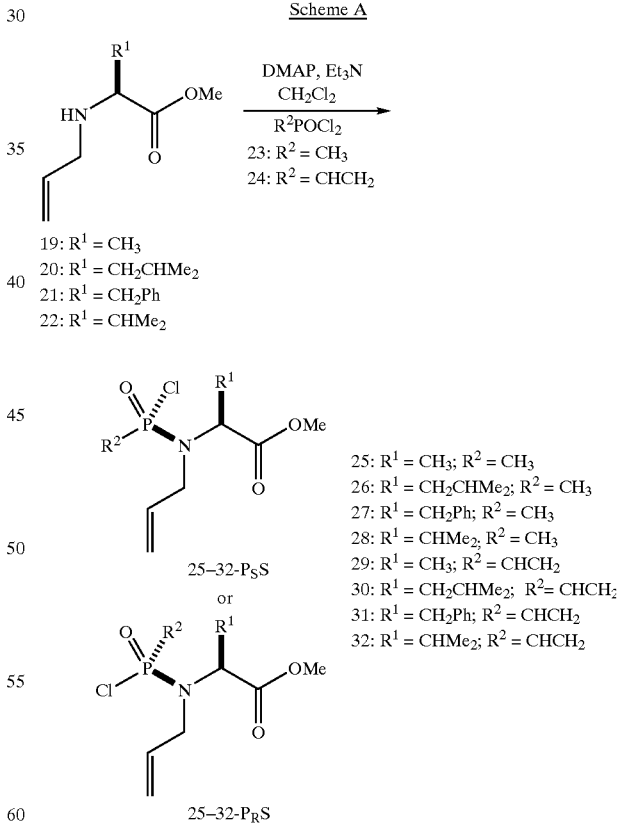

In this and the following procedure descriptions, the number/letter abbreviation depicted in the particular reaction scheme follows the chemical name of the particular compound (e.g., "(20)" follows "allylated leucine methyl ester").

I. Preparation of Leucine-Derived Methyl Phosphonamidic Chloridates ($26P_SS$ and $26P_RS$)

Methylphosphonic dichloride (23) (1.0 mL, 11.04 mmol) and $CH_2Cl_2$ (20 mL) were added to a flame-dried 100 mL round bottom flask under argon atmosphere. The reaction flask was cooled to 0° C., and $Et_3N$ (6.26 mL, 45.0 mmol) was added dropwise, followed by a catalytic amount of 4-dimethylaminopyridine (DMAP) (5 mol %). After stirring at 0° C. for 5 minutes, 0.98 equivalents of allylated leucine methyl ester (20) (2.0 g, 10.82 mmol) in $CH_2Cl_2$ (5 mL) was added via cannulae. The reaction mixture was refluxed and monitored by TLC. Once complete, the reaction mixture was concentrated under reduced pressure, diluted with EtOAc, filtered, and further concentrated under reduced pressure. Flash chromatography ($SiO_2$, 3:1 Hex/EtOAc) gave 2.94 g (95%) of a light yellow oil consisting solely of the two diastereomeric chloridates ($26P_SS$) and ($26P_RS$) (see Scheme B). Further chromatography ($SiO_2$, 8:1 Hex/EtOAc) yielded portions of the separated isomers for characterization.

Scheme B

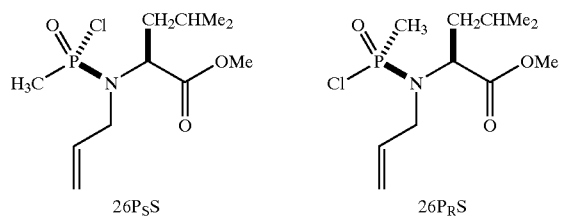

$26P_SS$        $26P_RS$

The leucine-derived methyl phosphonamidic chloridate ($26P_SS$ or $26P_RS$, top $R_f$) was characterized as follows: TLC $R_f$=0.39 (1:1 Hex:EtOAc); $[\alpha]^{25}$=−42.3 (c=2.44, $CHCl_3$);. FTIR 1742, 1445, 1368, 1240 (P=O) $cm^{-1}$; $^1H$ NMR (400 MHz, $CDCl_3$) δ5.78 (dddd, 16.9, 10.2, 6.5, 6.5 Hz, 1H), 5.22 (dd, J=17.2, 1.2 Hz, 1H), 5.14 (d, J=10.1 Hz, 1H), 4.40 (ddd, $J_{HP}$=12.1 Hz, $J_{HH}$=7.5, 7.5 Hz, 1H), 3.75–3.67 (m, 2H), 3.68 (s, 3H), 1.96 (d, $J_{HP}$=16.3 Hz, 3H), 1.70 (dd, J=7.3, 6.3 Hz, 2H), 1.65–1.52 (m, 1H), 0.91 (d, J=6.4Hz, 3H), 0.90 (d, J=6.5Hz, 3H); $^{13}C$ NMR (100 MHz, $CDCl_3$) δ172.37, 134.68 (d, $J_{CP}$=3.0 Hz), 118.04, 55.87, 52.05, 47.16 (d, $J_{CP}$=4.5 Hz), 38.49 (d, $J_{CP}$=5.7 Hz), 24.52, 22.65 (d, $J_{CP}$=118.9 Hz), 22.65, 21.53; $^{31}P$ NMR (162 MHz, $CDCl_3$) δ48.02; HRMS calculated for $C_{11}H_{23}ClNO_3P$ $(M+H)^+$ required 282.1026, found 282.1049.

The leucine-derived methyl phosphonamidic chloridates ($26P_RS$ or $26P_SS$, bottom $R_f$) were characterized as follows: TLC $R_f$=0.38(1:1 Hex:EtOAc); $[\alpha]^{25}$=−13.1 (c=1.44, $CHCl_3$); FTIR 1742, 1440, 1373, 1245 (P=O) $cm^{-1}$; $^1H$ NMR (400 MHz, $CDCl_3$) δ5.81–5.69 (m, 1H), 5.20–5.08 (m, 2H), 4.51 (ddd, $J_{HP}$=9.2 Hz, $J_{HH}$=6.2, 6.2 Hz, 1H), 3.76–3.66 (m, 2H), 3.62 (s, 3H), 1.98 (d, $J_{HP}$=16.0 Hz, 3H), 1.73–1.64 (m, 2H), 1.64–1.51 (m, 1H), 0.89 (d, J=6.3 Hz, 3H), 0.88 (d, J=6.5 Hz, 3H); $^{13}C$ NMR (100MHz, $CDCl_3$) δ172.56 (d, $J_{CP}$=6.2 Hz), 134.08 (d, $J_{CP}$=2.8 Hz), 118.06, 55.35 (d, $J_{CP}$=2.0 Hz), 51.97, 46.47 (d, $J_{CP}$=5.1 Hz), 37.14 (d, $J_{CP}$=2.1 Hz), 24.31, 22.80, 22.28 (d, $J_{CP}$=117.3 Hz), 21.20; $^{31}P$ NMR (162 MHz, $CDCl_3$) δ47.98; HRMS calculated for $C_{11}H_{23}ClNO_3P$ $(M+H)^+$ required 282.1026, found 282.1047.

II. Preparation of Leucine-Derived Vinyl Phosphonamidic Chloridates ($30P_SS$ and $30P_RS$)

$CH_2Cl_2$ (36 mL) and vinylphosphonic acid (1 mL, 12.86 mmol) were added to a flame-dried 100 mL round bottom flask under an inert atmosphere. The reaction mixture was stirred vigorously, and oxalyl chloride (3.36 mL, 38.6 mmol) was added followed by the addition of a catalytic amount of dimethyl formamide (DMF) (1 drop). The system was stirred for 2 hours (until gas evolution was no longer apparent). Upon completion of the reaction, the mixture was concentrated under reduced pressure to yield the vinylphosphonic dichloride (24) as a yellow oil. This oil was diluted with $CH_2Cl_2$ (20 mL) while precaution was taken to avoid exposure to moisture. The mixture was then cooled to 0° C. and $Et_3N$ (6.26 mL, 45.0 mmol) was added dropwise followed by DMAP (5 mol %). After stirring the reaction mixture at 0° C. for 5 minutes, allylated leucine methyl ester (20) (2.38 g, 12.86 mmol) in $CH_2Cl_2$ (5 mL) was added via cannulae. The reaction mix was refluxed and monitored by TLC. Once complete, the reaction mixture was concentrated under reduced pressure, diluted with EtOAc, filtered, and further concentrated under reduced pressure. Flash chromatography (3:1 Hexane/EtOAc) gave the two diastereomeric leucine-derived phosphonamidic chloridates ($30P_SS$ and $30P_RS$ (3.58 g, 95%) (see Scheme C) as a light yellow oil. These phosphonamidic chloridates were not further characterized.

Scheme C

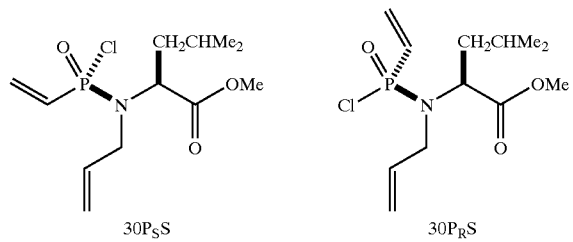

$30P_SS$        $30P_RS$

In Parts I–II of this procedure, methylene chloride was the solvent utilized. However, acetonitrile, chloroform, toluene, benzene, tetrahydrofuran (THF), diethyl ether, dimethoxyethane (DME), and mixtures thereof are also suitable solvents. Furthermore, while $Et_3N$ was used as the base, other bases which could be used include pyridine, $NaHCO_3$, $Na_2CO_3$, $K_2CO_3$, NaH, KH, any tertiary amine, and mixtures thereof. Finally, while the procedure was carried out at temperatures of 0–20° C., temperatures of anywhere from about −20–20° C. would also be suitable.

Example 2

Scheme D depicts the general overall reaction scheme followed in Parts I–VIII below, as well as the various compounds which can be prepared according to the procedure described in this example.

Scheme D

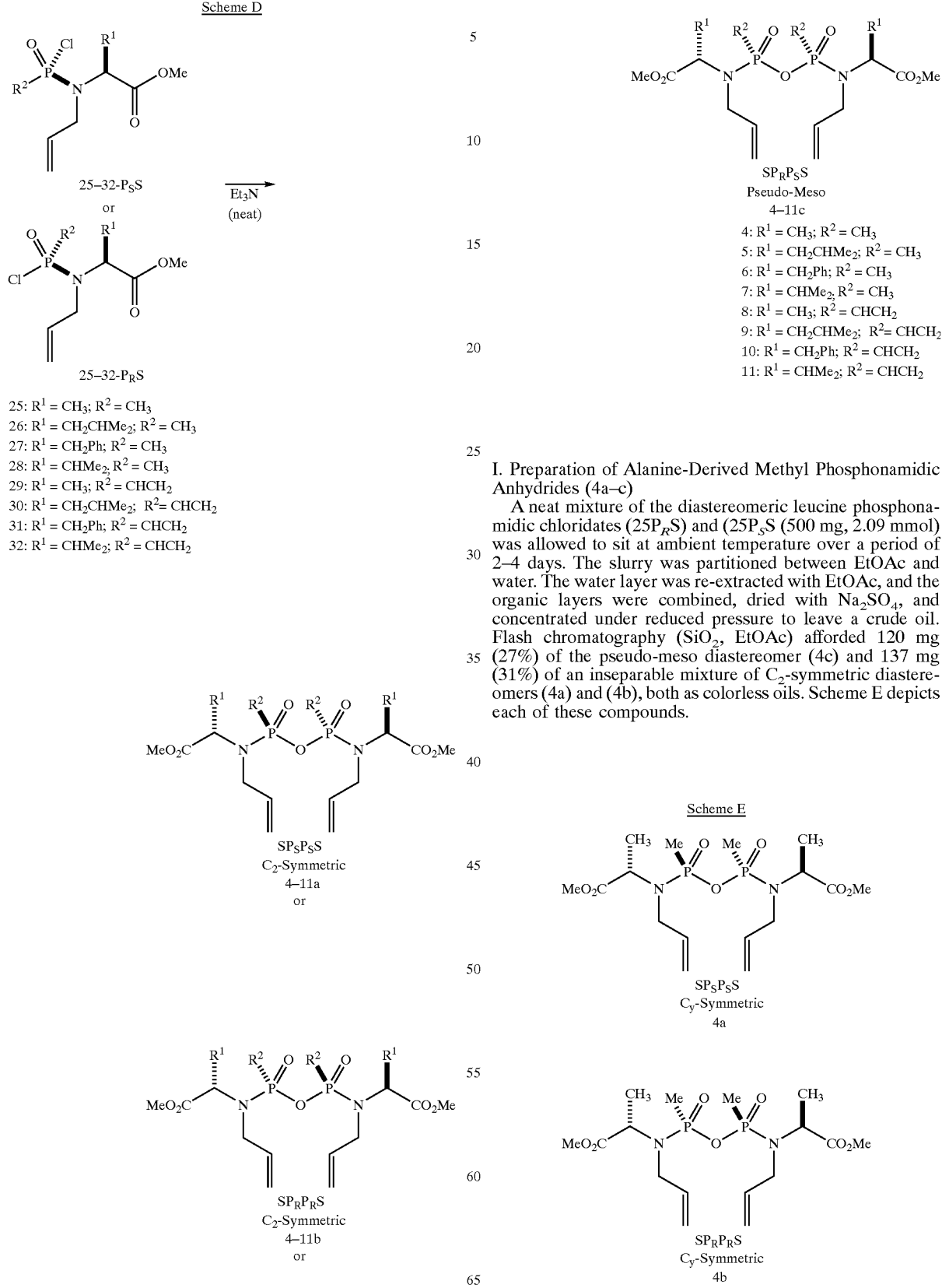

25–32-P$_S$S
or
25–32-P$_R$S

Et$_3$N (neat)

25: R$^1$ = CH$_3$; R$^2$ = CH$_3$
26: R$^1$ = CH$_2$CHMe$_2$; R$^2$ = CH$_3$
27: R$^1$ = CH$_2$Ph; R$^2$ = CH$_3$
28: R$^1$ = CHMe$_2$; R$^2$ = CH$_3$
29: R$^1$ = CH$_3$; R$^2$ = CHCH$_2$
30: R$^1$ = CH$_2$CHMe$_2$; R$^2$ = CHCH$_2$
31: R$^1$ = CH$_2$Ph; R$^2$ = CHCH$_2$
32: R$^1$ = CHMe$_2$; R$^2$ = CHCH$_2$

SP$_S$P$_S$S
C$_2$-Symmetric
4–11a
or

SP$_R$P$_R$S
C$_2$-Symmetric
4–11b
or

SP$_R$P$_S$S
Pseudo-Meso
4–11c

4: R$^1$ = CH$_3$; R$^2$ = CH$_3$
5: R$^1$ = CH$_2$CHMe$_2$; R$^2$ = CH$_3$
6: R$^1$ = CH$_2$Ph; R$^2$ = CH$_3$
7: R$^1$ = CHMe$_2$; R$^2$ = CH$_3$
8: R$^1$ = CH$_3$; R$^2$ = CHCH$_2$
9: R$^1$ = CH$_2$CHMe$_2$; R$^2$= CHCH$_2$
10: R$^1$ = CH$_2$Ph; R$^2$ = CHCH$_2$
11: R$^1$ = CHMe$_2$; R$^2$ = CHCH$_2$

I. Preparation of Alanine-Derived Methyl Phosphonamidic Anhydrides (4a–c)

A neat mixture of the diastereomeric leucine phosphonamidic chloridates (25P$_R$S) and (25P$_S$S (500 mg, 2.09 mmol) was allowed to sit at ambient temperature over a period of 2–4 days. The slurry was partitioned between EtOAc and water. The water layer was re-extracted with EtOAc, and the organic layers were combined, dried with Na$_2$SO$_4$, and concentrated under reduced pressure to leave a crude oil. Flash chromatography (SiO$_2$, EtOAc) afforded 120 mg (27%) of the pseudo-meso diastereomer (4c) and 137 mg (31%) of an inseparable mixture of C$_2$-symmetric diastereomers (4a) and (4b), both as colorless oils. Scheme E depicts each of these compounds.

Scheme E

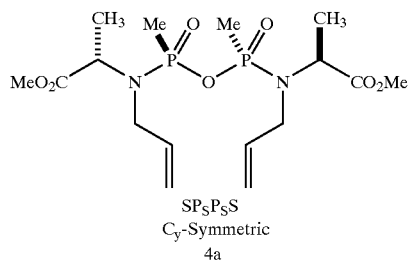

SP$_S$P$_S$S
C$_y$-Symmetric
4a

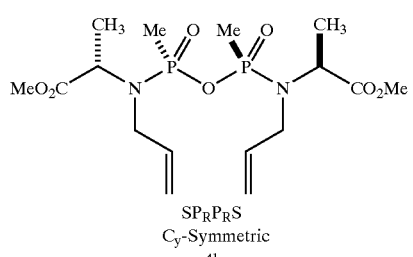

SP$_R$P$_R$S
C$_y$-Symmetric
4b

-continued

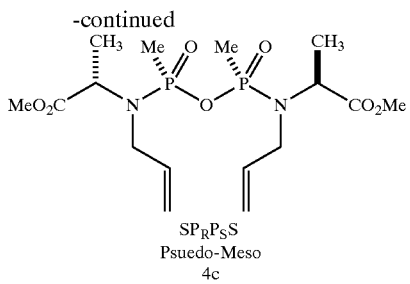

SP$_R$P$_S$S
Psuedo-Meso
4c

The C$_2$-symmetric alanine-derived methyl phosphonamidate anhydrides (4a,b) were characterized, as a mixture, as follows: TLC R$_f$=0.10 (EtOAc); FTIR 2992, 2951, 1740, 1457, 1437, 1382, 1232, 1170 cm$^{-1}$; $^1$H NMR (400 MHz, CDCl$_3$) δ5.82–5.72 (m, 4H, mix), 5.23–5.07 (m, 8H, mix), 4.54–4.48 (m, 2H, mix), 4.42–4.33 (m 2H, mix), 3.79–3.61 (m, 8H, mix), 3.67 (s, 6H), 3.66 (s, 6H), 1.73 (d, J$_{HP}$=16.6 Hz, 6H), 1.71 (d, J$_{HP}$=16.9 Hz, 6H), 1.43 (d, J=7.2 Hz, 6H), 1.42 (d, J=7.3 Hz, 6H); $^{13}$C NMR (100 MHz, CDCl$_3$) δ173.46, 173.20, 135.71, 135.33, 117.30, 117.08, 53.49, 52.99, 52.02, 52.02, 46.52, 46.32, 16.97, 16.10, 15.53 (dd, J$_{CP}$=137.7, 6.2 Hz), 14.99 (dd, J$_{CP}$=136.6, 4.6 Hz); $^{31}$P NMR (162 MHz, CDCl$_3$) δ29.47, 29.41; HRMS calculated for C$_{16}$H$_{31}$N$_2$O$_7$P$_2$ (M+H)$^+$ required 425.1614, found 425.1612.

The pseudo-meso alanine-derived methyl phosphonamidic anhydride (4c) was characterized as follow: TLC R$_f$=0.15 (EtOAc); [α]$^{25}$=–0.33 (c=0.60, CHCl$_3$); FTIR 2989, 2950, 1740, 1457, 1437, 1381, 1241 cm$^{-1}$; $^1$H NMR (400 MHz, CDCl$_3$) δ5.84–5.72 (m, 2H), 5.18 (dd, J=17.3, 1.3 Hz, 1H), 5.16 (dd, J=17.2, 1.3 Hz, 1H), 5.10–5.05 (m, 2H), 4.52 (dq, J$_{HP}$=11.1 Hz, J$_{HH}$=7.3 Hz, 1H), 4.23 (dq, J$_{HP}$=14.3 Hz, J$_{HH}$=7.1 Hz, 1H), 3.75–3.59 (m, 4H), 3.66 (s, 3H), 3.65 (s, 3H), 1.72 (d, J$_{HP}$=16.5 Hz, 3H), 1.66 (d, J$_{HP}$=16.6 Hz, 3H), 1.45 (d, J=7.2 Hz, 3H), 1.41 (d, J=7.3 Hz, 3H); $^{13}$C NMR (100 MHz, CDCl$_3$) δ173.48, 173.08, 135.35, 135.35, 117.40, 117.32, 53.90, 53.06, 52.02, 51.98, 47.14, 46.25, 17.05, 15.96, 15.23 (dd, J$_{CP}$=140.2, 6.5 Hz), 14.77 (dd, J$_{CP}$=139.6, 6.9 Hz); $^{31}$P NMR (162 MHz, CDCl$_3$) δ28.95 (d, J$_{PP}$=34.4 Hz), 28.94 (d, J$_{PP}$=34.4 Hz); HRMS calculated for C$_{16}$H$_{31}$N$_2$O$_7$P$_2$ (M+H)$^+$ required 425.1614, found 425.1606.

II. Preparation of Leucine-Derived Methyl Phosphonamidic Anhydrides (5a–c)

Et$_3$N (450 μL, 3.22 mmol) was added to a neat solution of a mixture of the diastereomeric leucine phosphonamidic chlorides (26P$_R$S) and (26P$_S$S) (260 mg, 0.92 mmol) at 0° C. The mixture was heated at 45° C. and monitored by TLC and $^{31}$P NMR. The resulting salty slurry was diluted with EtOAc (10 mL), filtered (10 mL), and concentrated under reduced pressure to yield 236 mg (quantitative) of a mixture of the three diastereomeric anhydrides as a yellow oil. Flash chromatography (SiO$_2$, 1:1 Hex/EtOAc) afforded 46 mg (20%) of the pseudo-meso diastereomer (5c) and 132 mg (56%) of a mixture of the C$_2$-symmetric diastereomers (5a) and (5b). The mixture comprised of 16 mg (7%) of a single C$_2$-symmetric diastereomer (5a) or (5b), 104 mg (44%) of a mixture of C$_2$-symmetric diastereomers (5a) and (5b), and 12 mg (5%) of a sample of C$_2$-symmetric diastereomer (5b) or (5a) at 90% purity, all as colorless oils.

The pseudo-meso leucine-derived methyl phosphonamidic anhydride (5c) was characterized as follows: TLC R$_f$=0.4 (EtOAc); [α]$^{25}$=–17.06 (c=0.59, CHCl$_3$); FTIR 1749, 1714, 1422, 1363, 1222 (P=O) cm$^{-1}$; $^1$H NMR (400 MHz, CDCl$_3$) δ5.87–5.75 (m, 2H), 5.18 (dd, J=17.1, 1.3 Hz, 1H), 5.14 (dd, J=17.1, 1.3 Hz, 1H), 5.12–5.06 (m, 2H), 4.49 (ddd, J$_{HP}$=10.7 Hz, J$_{HH}$=10.7, 5.4 Hz, 1H), 4.34 (ddd, J$_{HP}$=9.2 Hz, J$_{HH}$=9.2, 5.3 Hz, 1H), 3.75–3.58 (m, 4H), 3.68 (s, 3H), 3.66 (s, 3H), 1.83–1.60 (m, 6H), 1.74 (d, J$_{HP}$=16.8 Hz, 3H), 1.69 (d, J$_{HP}$16.7 Hz, 3H), 0.92 (d, J=6.2 Hz, 6H), 0.91 (d, J=6.2 Hz, 6H); $^{13}$C NMR (100 MHz, CDCl$_3$) δ173.67 (d, J$_{CP}$=2.2Hz), 173.20, 135.34, 135.34, 117.77, 117.48, 56.32 (d, J$_{CP}$=2.9 Hz), 55.93 (d, J$_{CP}$=3.6 Hz), 51.94, 51.90, 47.24 (d, J$_{CP}$=4.9 Hz), 46.45 (d, J$_{CP}$=4.9 Hz), 38.98 (d, J$_{CP}$=3.7 Hz), 37.57 (d, J$_{CP}$=2.6 Hz), 24.51, 24.19, 22.95, 22.87, 21.51, 21.33, 15.49 (dd, J$_{CP}$=129.5, 4.3 Hz), 14.80 (dd, J$_{CP}$=127.7, 4.5 Hz); $^{31}$P NMR (162 MHz, CDCl$_3$) δ29.19 (d, J$_{PP}$=35.5 Hz), 28.41 (d, J$_{PP}$=35.5 Hz); HRMS calculated for C$_{23}$H$_{43}$N$_2$O$_7$P$_2$ (M+H)$^+$ required 509.2546, found 509.2545.

The C$_2$-symmetric leucine-derived methyl phosphonamidic anhydride, single diastereomer (5a or 5b, top R$_f$) was characterized as follows: TLC R$_f$=0.22 (EtOAc); [α]$^{25}$=–37.8 (c=0.32, CHCl$_3$); FTIR 1740, 1437, 1387, 1241 (P=O) cm$^{-1}$; $^1$H NMR (400 MHz, CDCl$_3$) δ5.79 (dddd, J=16.9, 10.2, 6.2, 6.2 Hz, 2H), 5.21 (dd, J=15.9, 1.2 Hz, 2H), 5.12 (dd, J=9.8, 0.9 Hz, 2H), 4.49–4.42 (m, 2H), 3.79–3.57 (m, 4H), 3.67 (s, 6H), 1.81–1.59 (m, 6H), 1.75 (d, J$_{HP}$=17.0 Hz, 6H), 0.94 (d, J=6.0 Hz, 6H), 0.93 (d, J=6.2 Hz, 6H); $^{13}$C NMR (100 MHz, CDCl$_3$) δ173.33, 135.59, 117.62, 56.11, 51.95, 46.95, 38.71, 24.57, 22.94, 21.31, 15.67 (dd, J$_{CP}$=130.9, 5.6 Hz); $^{31}$P NMR (162 MHz, CDCl$_3$) δ29.88; HRMS calculated for C$_{23}$H$_{43}$N$_2$O$_7$P$_2$ (M+H)$^+$ required 509.2546, found 509.2526.

The C$_2$-symmetric leucine-derived methyl phosphonamidic anhydride, single diastereomer (5b or 5a, bottom R$_f$ at 90% purity) was characterized as follows: TLC R$_f$=0.22 (EtOAc); [α]$^{25}$=–5.0 (c=0.24, CHCl$_3$); FTIR 1740, 1437, 1387, 1241 (P=O) cm$^{-1}$; $^1$H NMR (400 MHz, CDCl$_3$) δ5.79 (dddd, J=16.8, 10.1, 6.6, 6.6 Hz, 2H), 5.17 (dd, J=16.7, 1.3 Hz, 2H), 5.10 (dd, J=9.1, 1.0 Hz, 2H), 4.52–4.42 (m, 2H), 3.66–3.54 (m, 4H), 3.68 (s, 6H), 1.80 (d, J$_{HP}$=15.8 Hz, 6H), 1.78–1.53 (m, 6H), 0.94 (d, J=6.0 Hz, 6H), 0.93 (d, J=6.2 Hz, 6H); $^{13}$C NMR (100 MHz, CDCl$_3$) δ173.48, 135.13, 117.47, 55.65, 51.91, 46.35, 37.46, 24.34, 22.99, 21.21, 15.27 (dd, J$_{CP}$=130.9, 5.6 Hz); $^{31}$P NMR (162 MHz, CDCl$_3$) δ30.14 HRMS calculated for C$_{23}$H$_{43}$N$_2$O$_7$P$_2$ (M+H)$^+$ required 509.2546, found 509.2561.

In this part of this example, Et$_3$N was used as the base. However, other bases could be used, including pyridine, NaHCO$_3$, Na$_2$CO$_3$, K$_2$CO$_3$, NaH, KH, any tertiary amine, and mixtures thereof. Finally, while the procedure was carried out at temperatures of 0–20° C., temperatures of from about –20–20° C. would also be suitable.

III Preparation of Phenylalanine-Derived Methyl Phosphonamidic Anhydrides (6a–c)

A mixture of the diastereomeric vinyl chloridates (27P$_S$S) and (27P$_R$S) (820 mg, 2.60 mmol) was subjected to the conditions described in Part I of this example. Flash chromatography (SiO$_2$, 1:1 Hex/EtOAc) afforded 195 mg (26%) of the pseudo-meso diastereomer (6c) and 172 mg (23%) of an inseparable mixture of C$_2$-symmetric diastereomers (6a) and (6b), both as colorless oils.

The pseudo-meso phenylalanine-derived methyl phosphonamidic anhydride (6c) was characterized as follows: TLC R$_f$=0.4 (EtOAc); [α]$^{25}$=–11.79 (c=0.60, CHCl$_3$); FTIR 1739, 1455, 1437, 1379, 1241, 1169 cm$^{-1}$; $^1$H NMR (400 MHz, CDCl$_3$) δ7.36–7.15 (m, 10H), 5.80–5.65 (m, 2H), 5.19 (dd, J=17.1, 0.9 Hz, 2H), 5.11 (d, J=10.1 Hz, 2H), 4.68 (ddd, J$_{HP}$=12.9 Hz, J$_{HH}$=9.6, 5.9 Hz, 1H), 4.64 (ddd, J$_{HHP}$=13.4 Hz, J$_{HH}$=10.0, 6.0 Hz, 1H), 3.69 (s, 3H), 3.68 (s, 3H), 3.65–3.61 (m, 2H), 3.61–3.42 (m, 2H), 3.35 (ddd, J$_{HH}$=14.3, 5.7 Hz, $J_{HP}$=5.7 Hz, 2H), 3.09 (ddd, J=14.4, 9.9, 2.8 Hz, 2H), 1.59 (d, $J_{HP}$=16.9 Hz, 3H), 0.97 (d, J=$J_{HP}$=16.8 Hz, 3H); $^{13}$C NMR (100 MHz, CDCl$_3$) δ172.41, 172.25, 137.62, 137.51, 134.75, 134.59, 129.35, 129.31, 128.38, 128.36, 128.26, 126.57, 126.50, 118.25, 117.98, 59.03 (d, $J_{CP}$=4.0 Hz), 58.96 (d, $J_{CP}$=4.1 Hz), 52.03, 51.96, 47.05 (d, $J_{CP}$=5.4 Hz), 46.90 (d, $J_{CP}$=4.9 Hz), 35.94, 35.30, 14.92 (d, $J_{CP}$=128.0 Hz), 14.00 (d, $J_{CP}$=126.6 Hz); $^{31}$P NMR (162 MHz, CDCl$_3$) 28.96 (d, $J_{pp}$=36.7 Hz), 28.12 (d, $J_{PP}$=36.7 Hz); HRMS calculated for C$_{28}$H$_{39}$N$_2$O$_7$P$_2$ (M+H)$^+$ required 577.2233, found 577.2232.

The C$_2$-symmetric phenylalanine-derived methyl phosphonamidic anhydride, single diastereomer (6a or 6b, top R$_f$) was characterized as follows (contamination with other diastereomer does not allow for optical rotation measurement): TLC R$_f$=0.15 (EtOAc); FTIR 1746, 1456, 1437, 1313, 1218, 737, 702 cm$^{-1}$; $^1$H NMR (400 MHz, CDCl$_3$) δ7.35–7.18 (m, 10H), 5.75–0.35 (m, 2H), 5.17–5.04 (m, 2H), 4.65–4.54 (m, 2H), 3.71–3.57 (m, 4H), 3.69 (s, 6H), 3.33–3.26 (m, 2H), 3.14–3.08 (m, 2H), 1.53 (d, $J_{HP}$=17.2 Hz, 6H); $^{13}$C NMR (100 MHz, CDCl$_3$) δ172.41, 137.45, 134.28, 129.12, 128.20, 126.27, 117.90, 58.33, 51.87, 46.90, 34.92, 15.13 (dd, $J_{CP}$=135.7, 4.3 Hz); $^{31}$P NMR (162 MHz, CDCl$_3$) δ29.36; LRMS calculated for C$_{28}$H$_{39}$N$_2$O$_7$P$_2$ (M+H)$^+$ required 577.6 found 577.6.

The C$_2$-symmetric phenylalanine-derived methyl phosphonamidate anhydride, single diastereomer (6a or 6b, bottom R$_f$) was characterized as follows (contamination with other diastereomer does not allow for optical rotation measurement): TLC R$_f$=0.15 (EtOAc); FTIR 1746, 1456, 1437, 1313, 1218, 737, 702 cm$^{-1}$; $^1$H NMR (400 MHz, CDCl$_3$) δ7.35–7.18 (m, 10H), 5.75–5.35 (m, 2H), 5.17 (d, J=17.1 Hz, 2H), 5.10 (d, J=10.5 Hz, 2H), 4.68–4.61 (m, 2H), 3.71–3.57 (m, 4H), 3.66 (s, 6H), 3.38–3.33 (m, 2H), 3.15–3.11 (m, 2H), 1.48 (d, $J_{HP}$=17.0 Hz, 6H); $^{13}$C NMR (100 MHz, CDCl$_3$) δ172.23, 137.45, 134.48, 129.08, 128.12, 126.44, 118.08, 58.90, 51.92, 47.40, 36.12, 14.96 (dd, $J_{CP}$=134.6, 4.4 Hz); $^{31}$P NMR (162 MHz, CDCl$_3$) δ30.10; LRMS calculated for C$_{28}$H$_{39}$N$_2$O$_7$P$_2$ (M+H)$^+$ required 577.6, found 577.6.

IV. Preparation of Valine-derived Methyl Phosphonamidic Anhydrides (7a–c)

A mixture of the diastereomeric vinyl chloridates (28P$_S$S) and (28P$_R$S) (505 mg, 1.89 mmol) was subjected to the conditions described in Part I of this example. Flash chromatography (SiO$_2$, 1:1 Hex/EtOAc) afforded 91 mg (20%) of the pseudo-meso diastereomer (7c) and 195 mg (43%) of an inseparable mixture of C$_2$-symmetric diastereomers (7a) and (7b), both as colorless oils.

The characterization of the pseudo-meso valine-derived methyl phosphonamidic anhydride (7c) was as follows: TLC R$_f$=0.20 (EtOAc); $[\alpha]^{25}$=−60.51 (c=0.43, CHCl$_3$); FTIR 1739, 1437, 1371, 1311, 1246, 1204 cm$^{-1}$; $^1$H NMR (400 MHz, CDCl$_3$) δ5.86–5.71 (m, 2H), 5.14 (dd, J=17.1, 1.3 Hz, 2H), 5.09–5.05 (m, 2H), 3.96–3.85 (m, 2H), 3.81–3.71 (m, 2H), 3.69–3.61 (m, 2H), 3.67 (s, 3H), 3.66 (s, 3H), 2.33–2.16 (m, 2H), 1.67 (d, $J_{HP}$=16.5 Hz, 3H), 1.65 (d, $J_{HP}$=16.6 Hz, 3H), 0.97 (d, J=6.7 Hz, 3H), 0.93 (d, J=6.7 Hz, 3H), 0.89 (d, J=6.6 Hz, 3H), 0.88 (d, J=6.5 Hz, 3H); $^{13}$C NMR (100 MHz, CDCl$_3$) δ172.12, 171.79, 135.18, 135.08, 117.67, 117.45, 63.51, 63.49, 51.57, 51.49, 46.44 (d, $J_{CP}$=3.9 Hz), 45.92 (d, $J_{CP}$=3.3 Hz), 27.59 (d, $J_{CP}$=3.0 Hz), 26.81, 19.72, 19.62, 19.39, 19.39, 15.60 (dd, $J_{CP}$=132.7, 8.8 Hz), 15.63 (dd, $J_{CP}$=134.8, 8.4 Hz); $^{31}$P NMR (162 MHz, CDCl$_3$) δ29.19 (d, $J_{PP}$=35.4 Hz), 28.4119 (d, $J_{PP}$=35.4 Hz). HRMS calculated for C$_{20}$H$_{39}$N$_2$O$_7$P$_2$ (M+H)$^+$ required 481.2233, found 481.2234.

Characterization of the C$_2$-symmetric valine-derived methyl phosphonamidate anhydride, single diastereomer (7a or 7b, top R$_f$) was as follows (contamination with other diastereomer does not allow for optical rotation measurement): TLC R$_f$=0.10 (EtOAc); FTIR 1739, 1436, 1370, 1309, 1245, 1204 cm$^{-1}$; $^1$H NMR (400 MHz, CDCl$_3$) δ5.76–5.61 (m, 2H), 5.10–5.01 (m, 4H), 3.86–3.80 (m, 2H), 3.78–3.42 (m, 4H), 3.60 (s, 6H), 2.25–2.13 (m, 2H), 1.70 (d, $J_{HP}$=16.7 Hz, 3H), 1.67 (d, $J_{HP}$=16.8 Hz, 3H), 0.90–0.83 (m, 12H); $^{13}$C NMR (100 MHz, CDCl$_3$) δ172.17, 134.91, 117.67, 63.37, 51.65, 45.91, 27.75, 26.91, 19.79, 16.03 (dd, $J_{CP}$=133.6, 3.8 Hz); $^{31}$P NMR (162 MHz, CDCl$_3$) δ30.20; LRMS calculated for C$_{20}$H$_{39}$N$_2$O$_7$P$_2$ (M+H)$^+$ required 480.1, found 480.1.

Characterization of the C$_2$-symmetric valine-derived methyl phosphonamidate anhydride, single diastereomer (7a or 7b, bottom R$_f$) was as follows (contamination with other diastereomer does not allow for optical rotation measurement): TLC R$_f$=0.10 (EtOAc); FTIR 1739, 1436, 1370, 1309, 1245, 1204 cm$^{-1}$; $^1$H NMR (400 MHz, CDCl$_3$) δ5.84–5.73 (m, 2H), 5.19 (dd, J=15.9, 1.1 Hz, 2H), 5.12 (d, J=8.8 Hz, 2H), 3.95–3.89 (m, 2H), 3.83–3.74 (m, 2H), 3.71–3.58 (m, 2H), 3.68 (s, 6H), 2.33–2.20 (m, 2H), 1.78 (d, $J_{HP}$=16.9 Hz), 1.75 (d, $J_{HP}$=17.1 Hz), 0.98–0.91 (m, 12H); $^{13}$C NMR (100 MHz, CDCl$_3$) δ172.16, 135.25, 117.77, 63.24, 51.62, 46.37, 27.75, 26.91, 19.72, 15.32 (dd, $J_{CP}$=134.3, 4.8 Hz); $^{31}$P NMR (162 MHz, CDCl$_3$) δ29.94; LRMS calculated for C$_{20}$H$_{39}$N$_2$O$_7$P$_2$ (M+H)$^+$ required 480.1, found 480.1.

V. Preparation of Alanine-Derived Vinyl Phosphonamidic Anhydrides (8a–c)

A mixture of the diastereomeric vinyl chloridates (29P$_S$S) and (29P$_R$S) (1.22 g, 4.86 mmol) was subjected to the conditions described in Part I of this example. Flash chromatography (SiO$_2$, 1:1 Hex/EtOAc) afforded 338 mg (31%) of the pseudo-meso diastereomer (8c) and 218 mg (20%) of an inseparable mixture of C$_2$-symmetric diastereomers (8a) and (8b), both as colorless oils.

The characterization of the pseudo-meso valine-derived vinyl phosphonamidic anhydride (8c) was as follows: TLC R$_f$=0.20 (EtOAc); $[\alpha]^{25}$=2.93 (c=0.82, CHCl$_3$); FTIR 1738, 1448, 1382, 1221, 1170 cm$^{-1}$; $^1$H NMR (400 MHz, CDCl$_3$) δ6.38–6.22 (m, 4H), 6.19–6.12 (m, 1H), 6.10–5.99 (m 1H), 5.82–5.69 (m, 2H), 5.14 (dd, J=17.1, 1.3 Hz, 1H), 5.11 (dd, J=17.2, 1.3 Hz, 1H), 5.07–5.02 (m, 2H), 4.45 (dq, $J_{HP}$=12.0 Hz, $J_{HH}$=7.3 Hz, 1H), 4.20 (dq, $J_{HP}$=14.4 Hz, $J_{HH}$=7.2 Hz, 1H), 3.70–3.62 (m, 4H), 3.64 (s, 3H), 3.63 (s, 3H), 1.44 (d, J=7.3 Hz, 3H), 1.40 (d, J=7.3 Hz, 3H); $^{13}$C NMR (100 MHz, CDCl$_3$) δ173.31 (d, $J_{CP}$=2.8 Hz), 173.00, 135.25, 135.10, 133.96, 133.64, 128.21 (dd, $J_{CP}$=180.3, 5.8 Hz), 127.09 (dd, $J_{CP}$=181.3, 5.2 Hz), 117.62, 117.58, 53.69 (d, $J_{CP}$=3.7 Hz), 52.79 (d, $J_{CP}$=4.1 Hz), 51.93, 51.89, 47.17 (d, $J_{CP}$=4.3 Hz), 46.41 (d, $J_{CP}$=4.3 Hz), 16.90, 15.76; $^{31}$P NMR (162 MHz, CDCl$_3$) δ16.40 (d, $J_{PP}$=34.5 Hz), 16.25 (d, $J_{PP}$=34.5 Hz); HRMS calculated for C$_{18}$H$_{31}$N$_2$O$_7$P$_2$ (M+H)$^+$ required 449.1607, found 449.1613.

The characterization of the C$_2$-symmetric alanine-derived vinyl phosphonamidic anhydride, single diastereomer (8a or 8b, top R$_f$) was as follows (contamination with other diastereomer does not allow for optical rotation measurement): TLC R$_f$=0.10 (EtOAc); FTIR 1741, 1450, 1382, 1224, 1170 cm$^{-1}$; $^1$H NMR (400 MHz, CDCl$_3$) δ6.41– 6.20 (m, 4H), 6.18–6.13 (m, 1H), 6.06–5.99 (m, 1H), 5.85–5.71 (m, 2H), 5.18 (d, J=17.2 Hz, 2H), 5.09 (d, J=10.4 Hz, 2H) 4.31–4.22 (m, 2H), 3.72–3.62 (m, 4H), 3.67 (s, 6H), 1.48 (d, J=7.3 Hz, 6H); $^{13}$C NMR (100 MHz, CDCl$_3$) δ173.39, 135.40, 133.99, 128.18 (dd, $J_{CP}$=173.2, 5.0 Hz), 117.54, 53.67, 51.99, 47.01, 16.94; $^{31}$P NMR (162 MHz, CDCl$_3$) δ16.69; LRMS calculated for C$_{18}$H$_{31}$N$_2$O$_7$P$_2$ (M+H)$^+$ required 449.4, found 449.4.

The characterization of the C$_2$-symmetric alanine-derived vinyl phosphonamidic anhydride, single diastereomer (8a or 8b, bottom R$_f$) was as follows (contamination with other diastereomer does not allow for optical rotation measurement): TLC R$_f$=0.10 (EtOAc); FTIR 1741, 1450, 1382, 1224, 1170 cm$^{-1}$; $^1$H NMR (400 MHz, CDCl$_3$) δ6.41–6.20 (m, 4H), 6.18–6.13 (m, 1H), 6.06–5.99 (m, 1H), 5.85–5.71 (m, 2H), 5.15 (d, J=16.9 Hz, 2H), 5.06 (d, J=11.0 Hz, 2H), 4.60–4.49 (m, 2H), 3.72–3.62 (m, 4H), 3.66 (s, 6H), 1.45 (d, J=7.3 Hz, 6H); $^{13}$C NMR (100 MHz, CDCl$_3$) δ173.39, 135.40, 134.11, 127.99 (d, J$_{CP}$=178.8 Hz), 117.46, 52.83, 51.94, 46.35, 15.97; $^{31}$P NMR (162 MHz, CDCl$_3$) δ16.70; LRMS calculated for C$_{18}$H$_{31}$N$_2$O$_7$P$_2$ (M+H)$^+$ required 449.4, found 449.4.

VI. Preparation of Leucine-Derived Vinyl Phosphonamidic Anhydrides (9a–c)

A mixture of the diastereomeric vinylchloridates (30P$_S$S) and (30P$_R$S) (355 mg, 1.21 mmol) was subjected to the conditions described in Part II of this example. Flash chromatography (SiO$_2$, 1:1 Hex/EtOAc) afforded 135 mg (42%) of the pseudo-meso diastereomer (9c) and 126 mg (39%) of an inseparable mixture of C$_2$-symmetric diastereomers (9a) and (9b), both as colorless oils.

The characterization of the pseudo-meso leucine-derived vinyl phosphonamidic anhydride (9c) was as follows: TLC R$_f$=0.68 (EtOAc); [α]$^{25}$=–15.59 (c=0.68, CHCl$_3$); FTIR 1740, 1649, 1461, 1438,1387, 1207 (P=O) cm$^{-1}$; $^1$H NMR (400 MHz, CDCl$_3$) δ6.45–6.22 (m, 4H), 6.19–6.11 (m, 1H), 6.06–5.98 (m, 1H), 5.82–5.72 (m, 2H), 5.13 (dd, J=17.1, 1.2 Hz, 2H), 5.09 (dd, J=17.1, 1.2 Hz, 2H), 4.46–4.40 (m, 1H), 4.33 (ddd, J=13.2, 9.5, 5.3 Hz, 1H), 3.64 (s, 3H), 3.64–3.59 (m, 4H), 3.63 (s, 3H), 1.79–1.56 (m, 6H), 0.88 (d, J=6.3 Hz, 6H), 0.87 (d, J=6.2 Hz, 6H); $^{13}$C NMR (100 MHz, CDCl$_3$) δ173.44 (d, J$_{CP}$=2.5 Hz), 173.14, 135.05, 135.05, 133.52, 133.52, 128.51 (dd, J$_{CP}$=166.4, 8.2 Hz), 128.33 (dd, J$_{CP}$=166.4, 9.0 Hz), 117.95, 117.68, 56.08 (d, J$_{CP}$=3.4 Hz), 55.68 (d, J$_{CP}$=4.3 Hz), 51.85, 51.76, 47.11 (d, J$_{CP}$=5.2 Hz), 46.52 (d, J$_{CP}$=5.2 Hz), 38.71 (d, J$_{CP}$=3.6 Hz), 37.61 (d, J$_{CP}$=3.0 Hz), 24.32, 24.06, 22.83, 22.83, 21.50, 21.34; $^{31}$P NMR (162 MHz, CDCl$_3$) δ16.48 (d, J$_{PP}$=37.5 Hz), 15.78 (d, J$_{PP}$=37.5 Hz); HRMS calculated for C$_{24}$H$_{43}$N$_2$O$_7$P$_2$ (M+H)$^+$ required 533.2546, found 533.2550.

Characterization of the C$_2$-symmetric leucine-derived vinyl phosphonamidic anhydrides (9a,b) as a mixture was as follows: TLC R$_f$=0.24 (EtOAc); FTIR 1741, 1642, 1613, 1469, 1438, 1370, 1233 (P=O), 1207 (P=O) cm$^{-1}$; $^1$H NMR (400 MHz, CDCl$_3$) δ6.37–6.21 (m, 8H), 6.08 (ddd, J=10.2, 8.6, 4.2 Hz, 2H), 5.94 (ddd, J=10.2, 8.5, 4.3 Hz, 2H), 5.75–5.65 (m, 4H), 5.11–4.96 (m, 8H), 4.40–4.29 (m, 4H), 3.65–3.51 (m, 8H), 3.57 (s, 6H), 3.56 (s, 6H), 1.74–1.49 (m, 12H), 0.87–0.81 (m, 24H); $^{13}$C NMR (100 MHz, CDCl$_3$) δ173.05, 172.93, 135.08, 135.01, 133.92, 133.86, 128.18 (dd, J$_{CP}$=176.8, 4.9 Hz), 127.98 (dd, J$_{CP}$=174.9, 4.1 Hz), 117.59, 117.33, 55.67, 55.50, 51.66, 51.60, 46.62, 46.22, 38.32, 37.49, 24.17, 23.98, 22.71, 22.71, 21.13, 21.05; $^{31}$P NMR (162 MHz, CDCl$_3$) δ17.46, 16.80; HRMS calculated for C$_{24}$H$_{43}$N$_2$O$_7$P$_2$ (M+H)$^+$ required 533.2546, found 533.2556.

VII. Preparation of Phenylalanine-Derived Vinyl Phosphonamidic Anhydrides (10a–c)

A mixture of the diastereomeric vinyl chlorides (31P$_S$S )and (31P$_R$S) (248 mg, 0.76 mmol) was subjected to the conditions described in Part I of this example. Flash chromatography (SiO$_2$, 1:1 Hex/EtOAc) afforded 61 mg (27%) of the pseudo-meso diastereomer (10c) and 64 mg (28%) of an inseparable mixture of C$_2$-symmetric diastereomers (10a) and (10b), both as colorless oils.

Characterization of the pseudo-meso phenylalaninevinyl phosphonamidic anhydride (10c) was as follows: TLC R$_f$=0.60 (EtOAc); [α]$^{25}$=–78.33 (c=0.66, CHCl$_3$); FTIR 1740, 1439, 1379, 1242, 1166, 750, 681 cm$^{-1}$; $^1$H NMR (400 MHz, CDCl$_3$) δ7.31–7.12 (m, 10H), 6.34–6.15 (m, 2H), 6.12–5.94 (m, 1H), 5.82–5.55 (m, 5H), 5.17 (dd, J=17.1, 1.0 Hz, 1H), 5.14 (dd, J=17.1, 1.1 Hz, 1H), 5.11–5.06 (m, 2H), 4.69–4.59 (m, 2H), 3.64 (s, 3H), 3.64 (s, 3H), 3.61–3.57 (m, 2H), 3.52–3.48 (m, 2H), 3.36 (dd, J=12.1, 6.6 Hz, 1H), 3.32 (dd, J=12.0, 6.5 Hz, 1H), 3.09 (dd, J=14.5, 7.8 Hz, 1H), 3.07 (dd, J=14.6, 8.0 Hz, 1H); $^{13}$C NMR (100 MHz, CDCl$_3$) δ172.24, 172.12, 137.52, 137.49, 134.57, 134.45, 133.66, 133.55, 129.27, 129.25, 128.32 (dd, J$_{CP}$=181.2, 7.2Hz), 128.30, 128.26, 127.17 (dd, J$_{CP}$=184.4, 6.1 Hz), 126.44, 126.42, 118.30, 118.22, 58.71, 58.49, 51.89, 51.77, 47.26, 47.02, 35.85, 35.71; $^{31}$P NMR (162 MHz, CDCl$_3$) δ15.90; HRMS calculated for C$_{30}$H$_{39}$N$_2$O$_7$P$_2$ (M+H)$^+$ required 601.2233, found 601.2233.

Characterization of the C$_2$-symmetric phenylalanine-derived vinyl phosphonamidic anhydride, single diastereomer (10a or 10b, top R$_f$) was as follows (contamination with other diastereomer does not allow for optical rotation measurement): TLC R$_f$=0.30 (EtOAc); FTIR 1740, 1437, 1239, 1168, 750, 681 cm$^{-1}$; $^1$H NMR (400 MHz, CDCl$_3$) δ7.28–7.09 (m, 10H), 6.18–5.43 (m, 8H), 5.16–5.01 (m, 4H), 4.71–4.63 (m, 1H), 4.54–4.46 (m, 1H), 3.59 (s, 6H), 3.55–3.47 (m, 2H), 3.36–3.26 (m, 4H), 3.13–3.03 (m, 2H); $^{13}$C NMR (100 MHz, CDCl$_3$) δ171.90, 137.31, 134.41, 133.63, 129.05, 128.05 (dd, J$_{CP}$=177.5, 4.4 Hz), 127.99, 126.18, 117.87, 58.64, 51.66, 47.18, 35.40; $^{31}$P NMR (162 MHz, CDCl$_3$) δ16.98; LRMS calculated for C$_{30}$H$_{39}$N$_2$O$_7$P$_2$ (M+H)$^+$ required 601.3, found 601.3.

The characterization of the C$_2$-symmetric phenylalanine-derived vinyl phosphonamidic anhydride, single diastereomer (10a or 10b, bottom R$_f$) yielded the following (contamination with other diastereomer does not allow for optical rotation measurement): TLC R$_f$=0.30 (EtOAc); FTIR 1740, 1437, 1239, 1168, 750, 681 cm$^{-1}$; $^1$H NMR (400 MHz, CDCl$_3$) δ7.28–7.09 (m, 10H), 6.18–5.43 (m, 8H), 5.16–5.01 (m, 4H), 4.71–4.63 (m, 1H), 4.54–4.46 (m, 1H), 3.58 (s, 6H), 3.55–3.47 (m, 2H), 3.36–3.26 (m, 4H), 3.13–3.03 (m, 2H); $^{13}$C NMR (100 MHz, CDCl$_3$) δ172.0 137.18, 134.45, 133.75, 128.96, 128.12, 127.39 (dd, J$_{CP}$=177.0, 4.6 Hz), 126.27, 117.96, 58.14, 51.64, 46.84, 35.69; $^{31}$P NMR (162 MHz, CDCl$_3$) δ17.56; LRMS calculated for C$_{30}$H$_{39}$N$_2$O$_7$P$_2$ (M+H)$^+$ required 601.3, found 601.3.

VIII. Preparation of Valine-derived Vinyl Phosphonamidic Anhydrides (11a–c)

A mixture of the diastereomeric vinyl chlorides (32P$_S$S) and (32P$_R$S) (734 mg, 2.63 mmol) was subjected to the conditions described in Part I of this example. Flash chromatography (SiO$_2$, 1:1 Hex/EtOAc) afforded 241 mg (40%) of the pseudo-meso diastereomer (11c) and 266 mg (44%) of an inseparable mixture of C$_2$-symmetric diastereomers (11a) and (11b), both as colorless oils.

The characterization of the pseudo-meso valine-derived vinyl phosphonamidic anhydride (11c) was as follows: TLC R$_f$=0.50 (EtOAc); [α]$^{25}$=–73.42 (c=0.54, CHCl$_3$); FTIR 1738, 1479, 1371, 1247, 1203 cm$^{-1}$; $^1$H NMR (400 MHz, CDCl$_3$) δ6.38–6.20 (m, 4H), 6.17–6.09 (m, 1H), 6.03–5.96 (m, 1H), 5.79 (dddd, J=16.9, 10.1, 6.8, Hz, 2H), 5.12 (d, J=17.1 Hz, 2H), 5.01 (dd, J=10.0, 1.5 Hz, 2H), 3.92 (t, J=11.3 Hz, 1H), 3.86 (t, J=11.0 Hz, 1H), 3.81–3.70 (m, 2H), 3.70–3.58 (m, 2H), 3.64 (s, 3H), 3.63 (s, 3H), 2.77–2.17 (m, 2H), 0.94 (d, J=6.7 Hz, 3H), 0.90 (d, J=6.7 Hz, 3H), 0.88 (d, J=6.4 Hz, 3H), 0.87 (d, J=6.4 Hz, 3H); $^{13}$C NMR (100 MHz, CDCl$_3$) δ172.02 (d, J$_{CP}$=2.9 Hz), 171.7 (d, J$_{CP}$=1.3 Hz), 135.14, 135.14, 134.07, 133.24, 128.75 (dd, J$_{CP}$=182.6, 9.0 Hz), 128.12 (dd, J$_{CP}$=183.9, 8.9 Hz), 117.67, 117.57, 63.71 (d, J$_{CP}$=4.1 Hz), 63.59 (d, J$_{CP}$=3.0 Hz), 51.40, 51.31, 46.45 (d, J$_{CP}$=4.8 Hz), 46.16 (d, J$_{CP}$=4.0 Hz), 27.71 (d, J$_{CP}$=3.3 Hz), 27.13 (d, J$_{CP}$=2.6 Hz), 19.77, 19.65, 19.59, 19.46; $^{31}$P NMR (162 MHz, CDCl$_3$) δ16.32 (d, J$_{PP}$=35. Hz), 15.98 (d, $J_{PP}$=35.9 Hz); HRMS calculated for $C_{22}H_{39}N_2O_7P_2$ (M+H)$^+$ required 505.2223, found 505.2227.

The characterization of the $C_2$-symmetric valine-derived vinyl phosphonamidic anhydride, single diastereomer (11a or 11b, top $R_f$) yielded the following (contamination with other diastereomer does not allow for optical rotation measurement): TLC $R_f$=0.40 (EtOAc); FTIR 1738, 1436, 1371, 1243, 1204cm$^{-1}$; $^1$H NMR (400 MHz, CDCl$_3$) δ6.36–6.22 (m, 4H), 6.19–6.10 (m, 1H), 6.03–5.97 (m, 1H), 5.82–5.71 (m, 2H), 5.15–5.02 (m, 4H), 3.94–3.87 (t, J=11.8 Hz, 1H), 3.83 (t, J=11.7 Hz, 1H), 3.79–3.67 (m, 2H), 3.69–3.57 (m, 2H), 3.64 (s, 6H), 2.30–2.17 (m, 2H), 0.90 (d, J=6.5 Hz, 6H), 0.87 (d, J=6.5 Hz, 6H); $^{13}$C NMR (100 MHz, CDCl$_3$) δ171.90, 135.06, 134.61, 127.88 (dd, $J_{CP}$=175.2, 4.6 Hz), 117.72, 63.34, 51.44, 46.25, 27.68, 19.67, 19.42; $^{31}$P NMR (162 MHz, CDCl$_3$) δ16.87; LRMS calculated for $C_{22}H_{39}N_2O_7P_2$ (M+H)$^+$ required 505.5, found 505.5.

Characterization of the $C_2$-symmetric valine-derived vinyl phosphonamidic anhydride, single diastereomer (11a or 11b, bottom $R_f$) resulted in the following (contamination with other diastereomer does not allow for optical rotation measurement): TLC $R_f$=0.40 (EtOAc); FTIR 1738, 1436, 1371, 1243, 1204 cm$^{-1}$; $^1$H NMR (400 MHz, CDCl$_3$) δ6.36–6.22 (m, 4H), 6.19–6.10 (m, 1H), 6.03–5.97 (m, 1H), 5.82–5.71 (m, 2H), 5.15–5.02 (m, 4H), 3.94–3.87 (t, J=11.8 Hz, 1H), 3.83 (t, J=11.7 Hz, 1H), 3.79–3.67 (m, 2H), 3.69–3.57 (m, 2H), 3.62 (s, 6H), 2.30–2.17 (m, 2H), 0.95 (d, J=6.6 Hz, 6H), 0.87 (d, J=6.5 Hz, 6H); $^{13}$C NMR (100 MHz, CDCl$_3$) δ171.90, 135.10, 134.02, 128.40 (dd, $J_{CP}$=174.5, 3.9 Hz), 117.56, 63.62, 51.39, 45.99, 27.09, 19.72, 19.53; $^{31}$P NMR (162 MHz, CDCl$_3$) δ17.20; LRMS calculated for $C_{22}H_{39}N_2O_7P_2$ (M+H)$^+$ required 505.5, found 505.5.

Example 3

Scheme F depicts the general overall reaction scheme followed in Parts I–II below, as well as the various compounds which can be prepared according to the procedure described in this example.

Scheme F

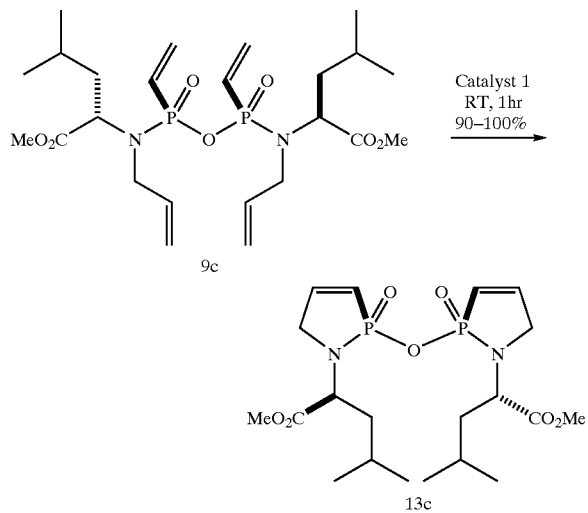

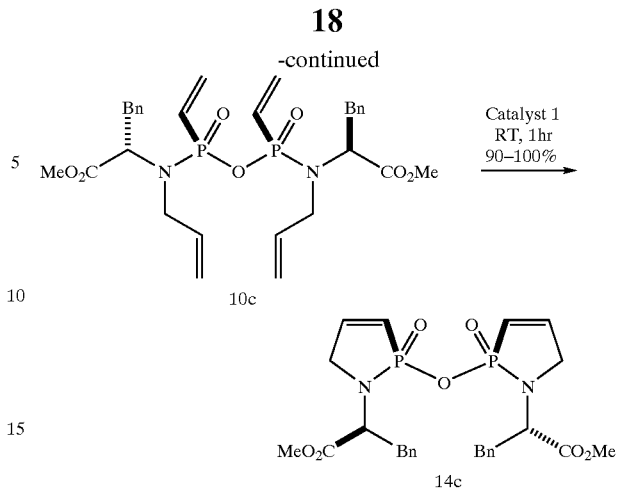

I. Preparation of Pseudo-meso Bicyclic Leucine-derived Phosphonamidic Anhydride (13c)

Leucine-derived vinyl phosphonamidic anhydride (9c) (88 mg, 0.165 mmol) and CH$_2$Cl$_2$ (15 mL) were added to a flame-dried 25 mL round bottom flask. The mixture was stirred, and the system was purged with argon for 10 minutes using a gas aerating tube. The Grubbs Catalyst 1 (6.8 mg, 8 μmol) was added under argon, and the reaction mixture was stirred and monitored for disappearance of the starting material. Upon completion, the reaction was concentrated under reduced pressure, passed through a plug of silica using EtOAc, and further concentrated under reduced pressure to give a crude oil. Flash chromatography (SiO$_2$, 100% EtOAc) afforded the bicyclic phosphonamidic anhydride (13c) (75 mg, 96%) (see Scheme G) as a colorless oil.

Scheme G

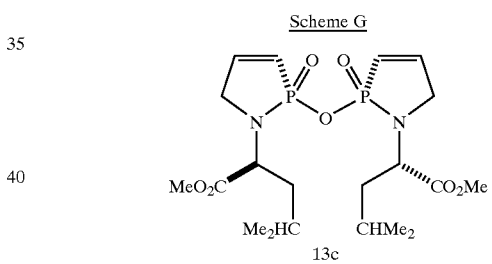

Characterization of the pseudo-meso bicyclic leucine-derived phosphonamidic anhydride (13c) was as follows: TLC $R_f$=0.20 (EtOAc); [α]$^{25}$=+11.1 (c 0.19, CHCl$_3$); FTIR 1742, 1587, 1451, 1390, 1346, 1241 (P=O), 1199 (P=O) cm$^{-1}$; H NMR (400 MHz, CDCl$_3$) δ7.11–7.06 (m, 1H), 7.00–6.95 (m, 1H), 6.25 (dd, J=30.3, 9.0 Hz, 1H), 6.12 (dd, J=30.2, 9.0 Hz, 1H), 4.47 (ddd, $J_{HP}$=9.4 Hz, $J_{HH}$=6.5, 6.5 Hz, 1H), 4.29 (ddd, $J_{HP}$=7.2 Hz, $J_{HH}$=7.2, 7.2 Hz, 1H), 4.17–4.06 (m, 2H), 3.76–3.67 (m, 2H), 3.67 (s, 3H), 3.65 (s, 3H), 1.67–1.64 (m, 4H), 1.64–1.51 (m, 2H), 0.97 (d, J=6.3 Hz, 3H), 0.93–0.90(m, 9H); $^{13}$C NMR(100 MHz, CDCl$_3$) δ173.60(d, $J_{CP}$=1.2 Hz), 173.13 (d, $J_{CP}$=1.9 Hz), 146.15 (d, $J_{CP}$=17.0 Hz), 145.75 (d, $J_{CP}$=17.4 Hz), 119.24 (d, $J_{CP}$=161.9 Hz), 118.62 (dd, $J_{CP}$=166.2, 2.9 Hz),52.20 (d, $J_{CP}$=4.1 Hz), 52.04(d, $J_{CP}$=4.5 Hz), 51.84, 51.73, 47.18 (d, $J_{CP}$=31.8 Hz), 46.82 (d, $J_{CP}$=31.1 Hz), 39.14 (d, $J_{CP}$=3.4 Hz), 38.49 (d, $J_{CP}$=3.8 Hz), 24.48, 24.47, 23.06, 22.99, 21.28, 21.07; $^{31}$P NMR (162 MHz, CDCl$_3$) δ33.55 (d, $J_{PP}$=24.0 Hz), 32.38 (d, $J_{PP}$=24.0 Hz); HRMS calculated for $C_{20}H_{35}N_2O_7P_2$ (M+H)$^+$ required 477.1919, found 477.1911.

II. Preparation of the Pseudo-meso Bicyclic Phenylalanine-Derived Phosphonamidic Anhydride (14c)

In a procedure similar to the preparation of the bicyclic leucine-derived phosphonamidic anhydrides (13c) as described in Part I of this example, compound (10c) (102 mg, 0.170 mmol) was subjected to Grubbs Catalyst 1 (7.0 mg, 8 μmol) in 15 mL $CH_2Cl_2$. Flash chromatography ($SiO_2$, 100% EtOAc) afforded (14c) (86 mg, 93%) (see Scheme H) as a colorless oil.

Scheme H

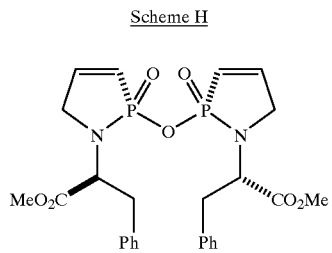

14c

Characterization of the resulting pseudo-meso bicyclic phenylalanine-derived phosphonamidic anhydride (14c) yielded the following: TLC $R_f$=0.37 (EtOAc); $[\alpha]^{25}$=−5.4 (c=0.74, $CHCl_3$); FTIR 2949, 2923, 2854, 1740, 1454, 1439, 1348, 1318, 1239, 1207, 1177, 901, 749, 698 cm$^{-1}$; $^1$H NMR (400 MHz, $CDCl_3$) δ7.32–7.18 (m, 10H), 7.08–7.03 (m, 1H), 6.96–6.91 (m, 1H), 6.21 (dd, $J_{HP}$=30.5 Hz, $J_{HH}$=9.0 Hz, 1H), 5.94 (dd, $J_{HP}$=30.2 Hz, $J_{HH}$=8.9 Hz, 1H), 4.66 (ddd, $J_{HP}$=7.7 Hz, $J_{HH}$=7.7, 7.7 Hz, 1H), 4.59 (ddd, $J_{HP}$=7.8 Hz, $J_{HH}$=7.8, 7.8 Hz, 1H), 4.16–4.09 (m, 2H), 3.88–3.77 (m, 2H), 3.63 (s, 3H), 3.86 (s, 3H), 3.32 (dd, J=14.1, 7.8, Hz, 1H), 3.27 (dd, J=13.3, 7.1 Hz, 1H), 3.09 (dd, J=13.7, 8.0 Hz, 1H), 3.03 (dd, J=14.0, 7.7 Hz, 1H); $^{13}$C NMR (100 MHz, $CDCl_3$) δ172.14, 171.95, 146.12 (d, $J_{CP}$=11.5 Hz), 145.95 (d, $J_{CP}$=11.7 Hz), 136.82, 136.26, 129.19, 128.79, 128.53, 128.46, 126.82, 126.77, 119.19 (d, $J_{CP}$=164.4 Hz), 118.7 (d, $J_{CP}$=163.7 Hz), 56.04 (d, $J_{CP}$=4.8 Hz), 55.00 (d, $J_{CP}$=4.3 Hz), 52.01, 51.91, 48.29 (d, $J_{CP}$=31.3 Hz), 47.62 (d, $J_{CP}$=30.9 Hz), 37.05, 36.58 (d, $J_{CP}$=3.7 Hz); $^{31}$P NMR (162 MHz, $CDCl_3$) δ33.21 (d, $J_{PP}$=24.9 Hz), 32.24 (d, $J_{PP}$=24.9 Hz); HRMS calculated for $C_{26}H_{31}N_2O_7P_2$ (M+H)$^+$ required 545.1606, found 545.1589.

In Parts I–II of this procedure, methylene chloride was the solvent utilized. However, toluene, benzene, chlorobenzene, dichlorobenzene, DME, and mixtures thereof are also suitable solvents. Furthermore, while Grubbs Catalyst 1 was used as the catalyst, it will be appreciated that Grubbs Catalyst 2 or 3 could also be utilized. Finally, while the procedure was carried out at a temperature of 40° C., temperatures of from about 15–80° C. would also be suitable.

We claim:

1. A compound having a formula selected from the group consisting of

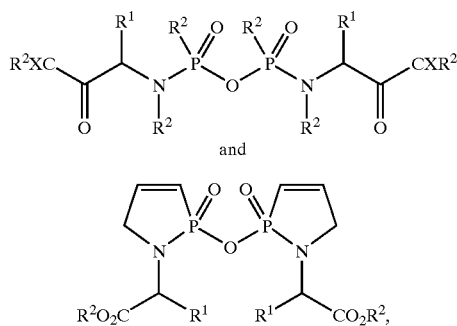

and wherein:
each X is individually selected from the group consisting of oxygen, —NH, and —NOR$^1$;

each R$^1$ is individually selected from the group consisting of hydrogen, a 2–15 mer peptide, and an amino acid side chain selected from the group consisting of

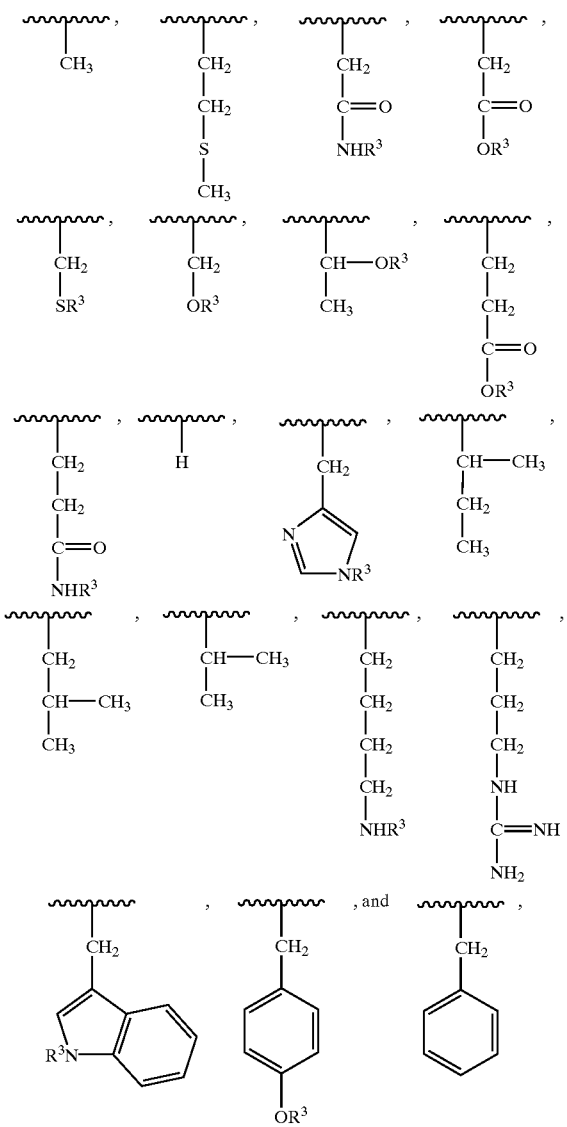

wherein
each R$^3$ is individually selected from the group consisting of hydrogen, a branched alkyl group, an unbranched alkyl group, a branched alkenyl group, an unbranched alkenyl group, a branched alkynyl group, an unbranched alkynyl group, an allyl group, an aryl group, an acyl group, and a benzyl group; and
each R$^2$ is individually selected from the group consisting of hydrogen, a branched alkyl group, an unbranched alkyl group, a branched alkenyl group, an unbranched alkenyl group, a branched alkynyl group, an unbranched alkynyl group, an allyl group, an aryl group, an acyl group, a 2–15 mer peptide, and a benzyl group.

2. The compound of claim 1, wherein:
each R$^1$ is individually selected from the group consisting of —CH$_3$, —CH$_2$CH(R$^4$)$_2$, —CH$_2$R$^4$, and —CH(R$^4$)$_2$, with each R$^4$ being individually selected from the group consisting of an alkyl group, an aryl group, and a benzyl group; and each R² is individually selected from the group consisting of —CH₃ and —CHCH₂.

3. The compound of claim 2, wherein each R⁴ is individually selected from the group consisting of a methyl group and a phenyl group.

4. The compound of claim 1, wherein said compound has a formula selected from the group consisting of

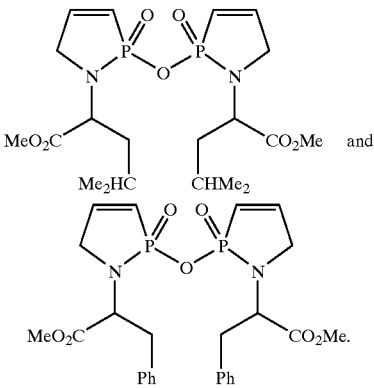

and

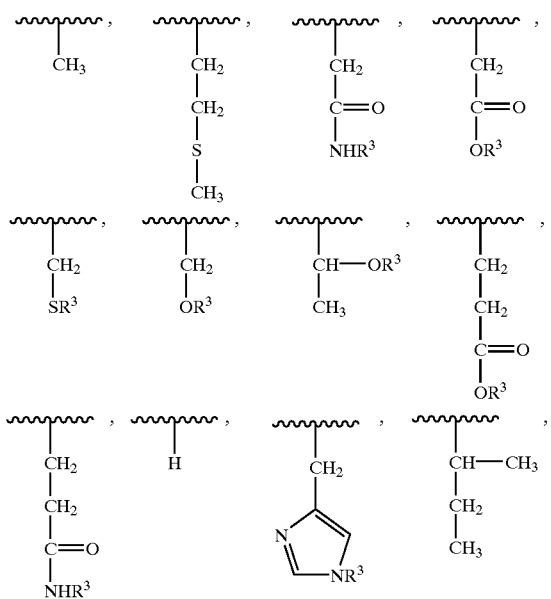

5. A method of forming a phosphonamide compound comprising the steps of:
reacting an allylated compound with a phosphonic compound in order to form an intermediate compound, said allylated compound having the formula

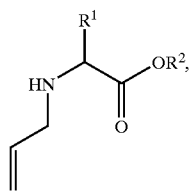

wherein:
R¹ is selected from the group consisting of hydrogen, a 2–15 mer peptide, and an amino acid side chain selected from the group consisting of

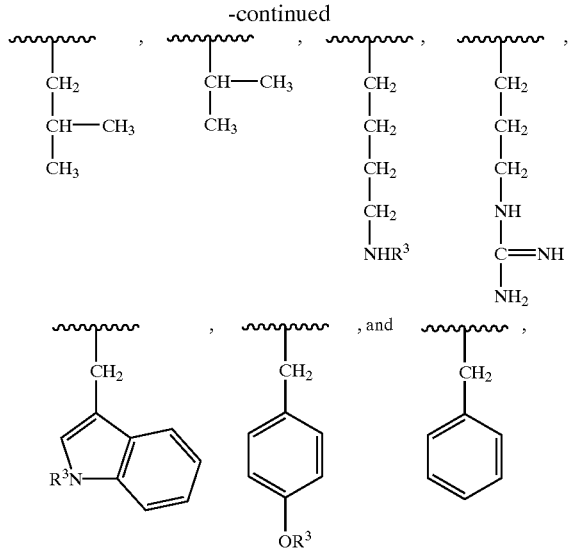

wherein each R³ is individually selected from the group consisting of hydrogen, a branched alkyl group, an unbranched alkyl group, a branched alkenyl group, an unbranched alkenyl group, a branched alkynyl group, an unbranched alkynyl group, an allyl group, an aryl group, an acyl group, and a benzyl group; and R² is selected from the group consisting of hydrogen, a branched alkyl group, an unbranched alkyl group, a branched alkenyl group, an unbranched alkenyl group, a branched alkynyl group, an unbranched alkynyl group, an allyl group, an aryl group, an acyl group, a 2–15 mer peptide, and a benzyl group, and said phosphonic compound having the formula R⁴POY₂, wherein:
R⁴ is selected from the group consisting of hydrogen, a branched alkyl group, an unbranched alkyl group, a branched alkenyl group, an unbranched alkenyl group, a branched alkynyl group, an unbranched alkynyl group, an allyl group, an aryl group, an acyl group, a 2–15 mer peptide, and a benzyl group; and each Y is individually selected from the group consisting of the halogens; and dimerizing said intermediate compound to yield the phosphonamide compound.

6. The method of claim 5, wherein said allylated compound has the formula

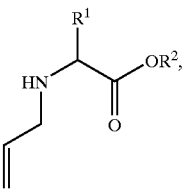

wherein R¹ is selected from the group consisting of —CH₃, —CH₂CHMe₂, —CH₂Ph, and —CHMe₂, and R² is an alkyl group.

7. The method of claim 5, wherein said phosphonic compound has the formula R⁴POCl₂, wherein R⁴ is selected from the group consisting of —CH₃ and —CHCH₂.

8. The method of claim 5, wherein said intermediate compound has the formula

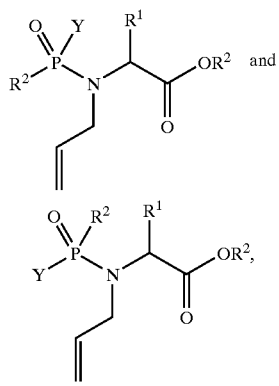

wherein:

R¹ is selected from the group consisting of hydrogen, a 2–15 mer peptide, and an amino acid side chain selected from the group consisting of

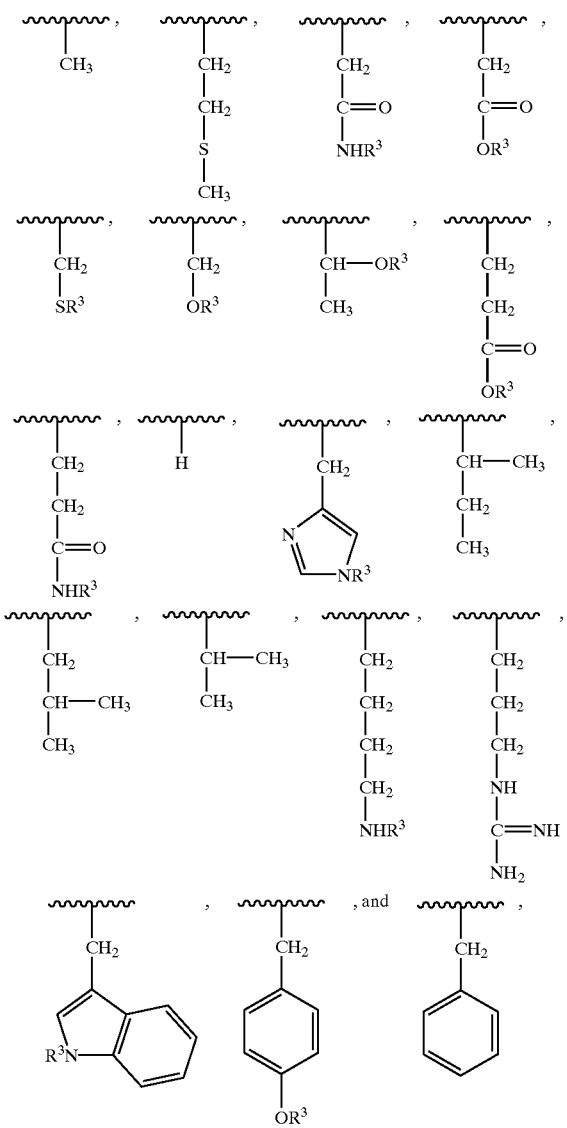

wherein each R³ is individually selected from the group consisting of hydrogen, a branched alkyl group, an unbranched alkyl group, a branched alkenyl group, an unbranched alkenyl group, a branched alkynyl group, an unbranched alkynyl group, an allyl group, an aryl group, an acyl group, and a benzyl group; and each R² is individually selected from the group consisting of hydrogen, a branched alkyl group, an unbranched alkyl group, a branched alkenyl group, an unbranched alkenyl group, a branched alkynyl group, an unbranched alkynyl group, an allyl group, an aryl group, an acyl group, a 2–15 mer peptide, and a benzyl group; and each Y is individually selected from the group consisting of the halogens.

9. The method of claim 5, wherein said phosphonamide compound has the formula

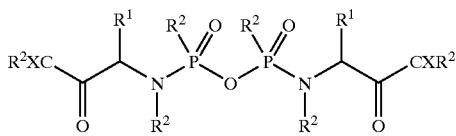

wherein:

each X is individually selected from the group consisting of oxygen, —NH, and —NOR¹;

each R¹ is individually selected from the group consisting of hydrogen, a 2–15 mer peptide, and an amino acid side chain selected from the group consisting of

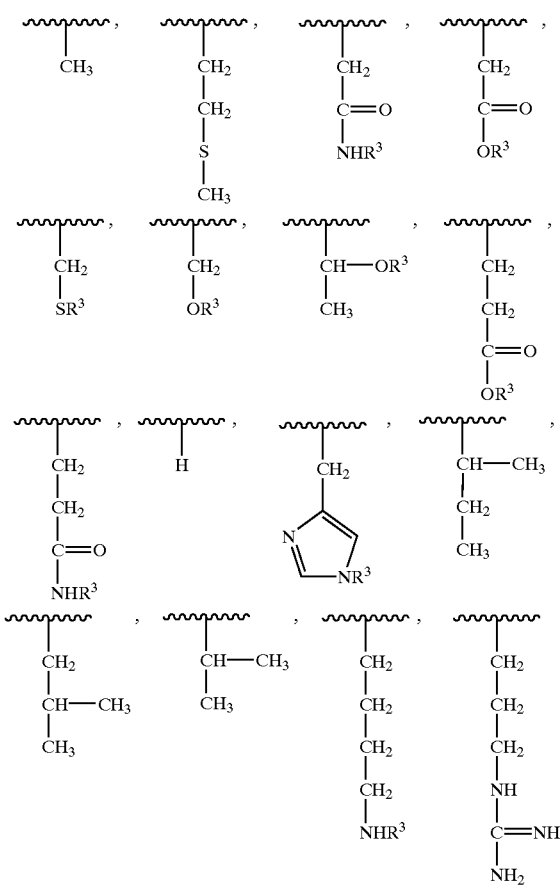

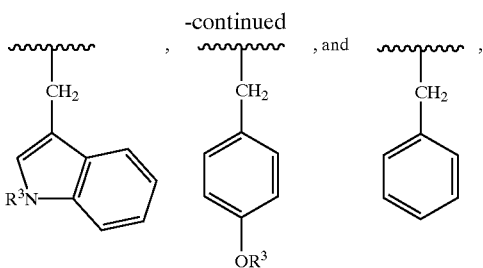

wherein each R³ is individually selected from the group consisting of hydrogen, a branched alkyl group, an unbranched alkyl group, a branched alkenyl group, an unbranched alkenyl group, a branched alkynyl group, an unbranched alkynyl group, an allyl group, an aryl group, an acyl group, and a benzyl group; and each R² is individually selected from the group consisting of hydrogen, a branched alkyl group, an unbranched alkyl group, a branched alkenyl group, an unbranched alkenyl group, a branched alkynyl group, an unbranched alkynyl group, an allyl group, an aryl group, an acyl group, a 2–15 mer peptide, and a benzyl group.

10. The method of claim 5, wherein said reacting step is carried out in the presence of a compound selected from the group consisting of a base, a catalyst, and a solvent.

11. The method of claim 10, wherein said compound is a base selected from the group consisting of Et₃N, pyridine, NaHCO₃, Na₂CO₃, K₂CO₃, NaH, KH, and mixtures thereof.

12. The method of claim 10, wherein said compound is a catalyst and said catalyst is 4-dimethylaminopyridine.

13. The method of claim 10, wherein said compound is a solvent selected from the group consisting of acetonitrile, chloroform, toluene, benzene, tetrahydrofuran, diethyl ether, dimethoxyethane, and mixtures thereof.

14. The method of claim 5, wherein said reacting step and said dimerizing step are each individually carried out at a temperature of from about –20–20° C.

15. The method of claim 5, wherein said reacting step is carried out in the presence of a base.

16. The method of claim 15, wherein said base is selected from the group consisting of Et₃N, pyridine, NaHCO₃, Na₂CO₃, K₂CO₃, NaH, KH, and mixtures thereof.

17. The method of claim 5, further including the step of reacting said phosphonamide compound with a ring-closing catalyst to yield a bicyclic phosphonamide.

18. The method of claim 17, wherein said ring-closing catalyst is a Grubbs catalyst.

19. The method of claim 18, wherein said Grubbs catalyst is selected from the group consisting of

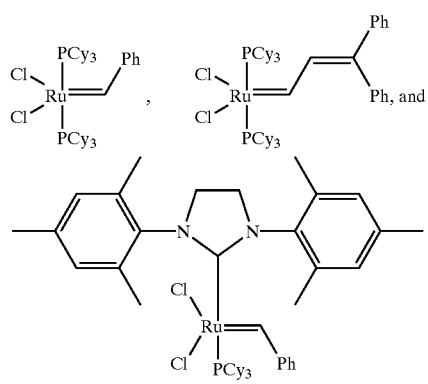

20. The method of claim 17, wherein said bicyclic phosphonamide has the formula

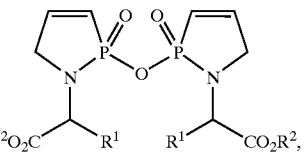

wherein:
each R¹ is individually selected from the group consisting of hydrogen, a 2–15 mer peptide, and an amino acid side chain selected from the group consisting of

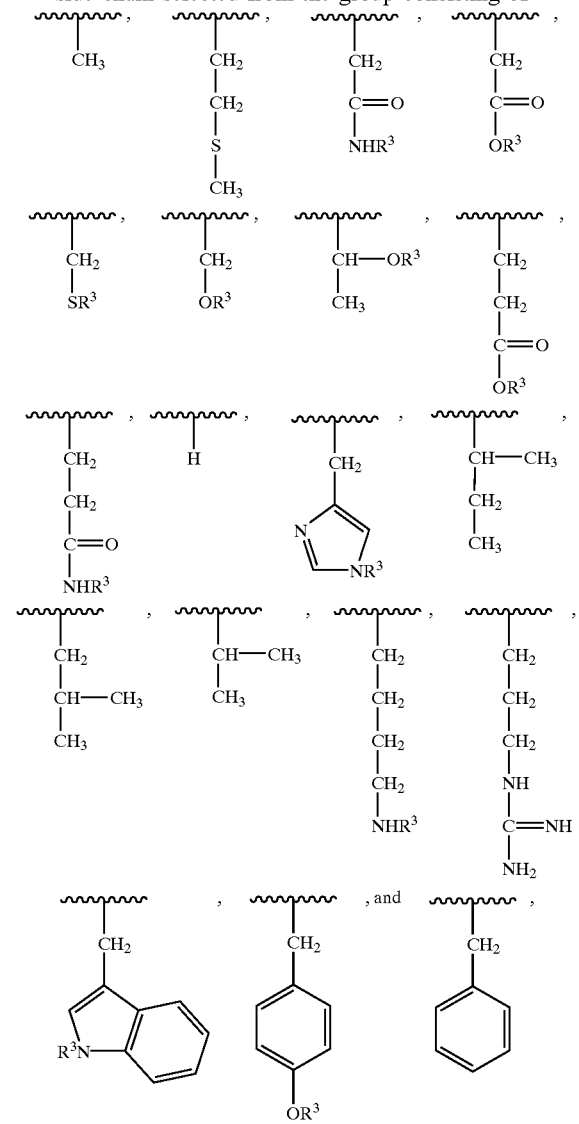

wherein each R³ is individually selected from the group consisting of hydrogen, a branched alkyl group, an unbranched alkyl group, a branched alkenyl group, an unbranched alkenyl group, a branched alkynyl group, an unbranched alkynyl group, an allyl group, an aryl group, an acyl group, and a benzyl group; and each R² is individually selected from the group consisting of hydrogen, a branched alkyl group, an unbranched alkyl group, a branched alkenyl group, an unbranched alkenyl group, a branched alkynyl group, an unbranched alkynyl group, an allyl group, an aryl group, an acyl group, a 2–15 mer peptide, and a benzyl group.

* * * * *